United States Patent
Mok et al.

(10) Patent No.: US 10,354,427 B2
(45) Date of Patent: Jul. 16, 2019

(54) METHOD OF DRIVING HEAD MOUNTED DISPLAY AND HEAD MOUNTED DISPLAY PERFORMING THE SAME

(71) Applicant: Samsung Display Co., LTD., Gyeonggi-Do (KR)

(72) Inventors: Rang-Kyun Mok, Seoul (KR); Hyo-Sun Kim, Gyeonggi-do (KR); Young-Jun Seo, Seoul (KR); Il-Nam Kim, Gyeonggi-do (KR); Seock-Hwan Kang, Seoul (KR); Ji-Young Moon, Gyeonggi-do (KR); Won-Sang Park, Gyeonggi-do (KR); Yun-Taek Kim, Seoul (KR)

(73) Assignee: Samsung Display Co., Ltd. (KR)

( * ) Notice: Subject to any disclaimer, the term of this patent is extended or adjusted under 35 U.S.C. 154(b) by 21 days.

(21) Appl. No.: 15/661,171

(22) Filed: Jul. 27, 2017

(65) Prior Publication Data
US 2018/0108161 A1   Apr. 19, 2018

(30) Foreign Application Priority Data
Oct. 19, 2016   (KR) .......................... 10-2016-0136018

(51) Int. Cl.
| | |
|---|---|
| *G06T 11/60* | (2006.01) |
| *A61B 3/00* | (2006.01) |
| *A61B 3/08* | (2006.01) |
| *G06T 3/20* | (2006.01) |
| *G06T 3/40* | (2006.01) |

(Continued)

(52) U.S. Cl.
CPC ............... *G06T 11/60* (2013.01); *A61B 3/08* (2013.01); *G06T 3/20* (2013.01); *G06T 3/40* (2013.01); *G06T 11/001* (2013.01); *H04N 13/128* (2018.05); *H04N 13/344* (2018.05)

(58) Field of Classification Search
CPC .......... A61B 3/113; A61B 5/162; A61B 5/16; A61B 5/6803; A61B 3/0041; A61B 3/0091; A61B 3/02; A61B 3/152; A61B 3/024; A61B 5/04525; G02B 27/0093; G02B 27/017; G02B 2027/0198; G02B 27/01

See application file for complete search history.

(56) References Cited

U.S. PATENT DOCUMENTS

| | | | |
|---|---|---|---|
| 5,491,492 A | 2/1996 | Knapp et al. | |
| 7,328,116 B2 * | 2/2008 | Bala ...................... | H04N 17/04 348/E17.005 |

(Continued)

FOREIGN PATENT DOCUMENTS

KR   10-1370588 B1   3/2014

*Primary Examiner* — Sultana M Zalalee
(74) *Attorney, Agent, or Firm* — Innovation Counsel LLP

(57) ABSTRACT

A method of driving a head mounted display is provided. The method derives a position adjustment data by displaying a binocular position adjustment image on a left-eye panel region and a right-eye panel region, derives a size adjustment data by displaying a binocular size adjustment image on the left-eye panel region and the right-eye panel region, generates a luminance adjustment data based on a difference between a left-eye and a right-eye luminance perception data, converts an image source into an input image data based on the position adjustment data, the size adjustment data, and the luminance adjustment data, and displays an image corresponding to the input image data.

17 Claims, 19 Drawing Sheets

(51) Int. Cl.
  *G06T 11/00* (2006.01)
  *H04N 13/344* (2018.01)
  *H04N 13/128* (2018.01)

(56) References Cited

U.S. PATENT DOCUMENTS

| | | | | |
|---|---|---|---|---|
| 8,094,927 | B2* | 1/2012 | Jin | H04N 13/122 |
| | | | | 382/154 |
| 9,706,910 | B1* | 7/2017 | Blaha | A61B 3/032 |
| 2009/0141121 | A1* | 6/2009 | Kimpe | H04N 13/0425 |
| | | | | 348/51 |
| 2010/0073469 | A1* | 3/2010 | Fateh | A61H 5/00 |
| | | | | 348/62 |
| 2011/0075099 | A1* | 3/2011 | Kanazawa | A61B 3/0285 |
| | | | | 351/232 |
| 2013/0002660 | A1* | 1/2013 | Chikazawa | G02B 27/2264 |
| | | | | 345/419 |
| 2013/0044290 | A1* | 2/2013 | Kawamura | A61B 3/032 |
| | | | | 351/201 |
| 2013/0100400 | A1* | 4/2013 | Hofeldt | A61B 3/08 |
| | | | | 351/201 |
| 2014/0347252 | A1* | 11/2014 | Miyawaki | G02B 27/017 |
| | | | | 345/8 |
| 2015/0351625 | A1* | 12/2015 | Schroth | A61B 3/085 |
| | | | | 351/201 |
| 2016/0180503 | A1* | 6/2016 | Frascati | G06T 3/0093 |
| | | | | 345/646 |
| 2017/0049316 | A1* | 2/2017 | Donaldson | A61B 3/024 |
| 2018/0104106 | A1* | 4/2018 | Lee | A61F 9/08 |

* cited by examiner

METHOD OF DRIVING HEAD MOUNTED DISPLAY AND HEAD MOUNTED DISPLAY PERFORMING THE SAME

CROSS REFERENCE TO RELATED APPLICATION

This application claims priority under 35 U.S.C. § 119 to Korean patent Application No. 10-2016-0136018 filed on Oct. 19, 2016, the disclosure of which is hereby incorporated by reference herein in its entirety.

BACKGROUND

1. Technical Field

Example embodiments of the inventive concept relate to display devices. More particularly, example embodiments of the inventive concept relate to a method of driving head mounted display and a head mounted display performing the method.

2. Description of the Related Art

A head mounted display may be mounted on a user's head, may enlarge an image (e.g., an image displayed on a display panel) using a lens, and may provide the image directly to eyes of the user.

Generally, when a pixel density of a display panel is greater than 500 pixels per inch (PPI), the user may not recognize pixels in the normal display panel. However, the user could recognize pixels in the display panel of the head mounted display because the head mounted display provide magnified images to the user using the lens. The head mounted display may perform a variety of image processing methods for improving a display quality such as a rendering process in the boundary of the object in the image, etc.

However, since the head mounted display does not consider the difference in the visual perceptions of the user's left-eye and right-eye (hereinafter, referred to as "binocular disparity") in the image processing process, the perceived fatigue of the user is increased and the nausea (or motion sickness) caused by sensory conflict of the binocular vision can be felt. If the user has a binocular vision dysfunction such as strabismus, amblyopia, anisometropia, or aniseikonia, the user may feel discomfort or may not feel VR (virtual reality) experience normally when the user uses the head mounted display for the VR experience.

SUMMARY

Example embodiments provide a method of driving a head mounted display capable of reducing the user's fatigue.

Example embodiments provide a head mounted display performing the method of driving the head mounted display.

According to some example embodiments, a method of driving a head mounted display may include an operation of deriving a position adjustment data by displaying a binocular position adjustment image on a left-eye panel region and a right-eye panel region, an operation of deriving a size adjustment data by displaying a binocular size adjustment image on the left-eye panel region and the right-eye panel region, an operation of generating a luminance adjustment data based on a difference between a left-eye luminance perception data and a right-eye luminance perception data, an operation of converting an image source into an input image data based on at least one of the position adjustment data, the size adjustment data, or the luminance adjustment data, and an operation of displaying an image corresponding to the input image data on the left-eye panel region and the right-eye panel region.

In example embodiments, the method of driving a head mounted display may further include an operation of displaying a binocular balancing image on the left-eye panel region and the right-eye panel region. The binocular balancing image may include a first left-eye image and a first right-eye image, the first left-eye image including a fir left-eye object and displayed on the left-eye panel region, the first right-eye image including a first right-eye object and displayed on the right-eye panel region.

In example embodiments, the operation of the deriving the position adjustment data may include an operation of displaying a second left-eye image including a second left-eye object on the left-eye panel region and a second right-eye image including a second right-eye object on the right-eye panel region, an operation of moving at least one of the second left-eye image or the second right-eye image in a first direction or a second direction orthogonal to the first direction based on an input signal received from an input device, and an operation of generating the position adjustment data based on a moved position to which the at least one of the second left-eye image or the second right-eye image is moved.

In example embodiments, a first color of the second left-eye object may be complementary to a second color of the second right-eye object.

In example embodiments, the second left-eye object and the second right-eye object may have different sizes and may have shapes substantially the same to each other.

In example embodiments, the second left-eye object and the second right-eye object may be symmetrical with each other and may have the same size.

In example embodiments, the second left-eye image may further include a first guide object of which position does not changed regardless of the input signal. The second right-eye image may further include a second guide object of which position does not changed regardless of the input signal. The first guide object and the second guide object may be disposed at positions corresponding to each other.

In example embodiments, the operation of the deriving the size adjustment data may include an operation of displaying a third left-eye image including a third left-eye object on the left-eye panel region and a third right-eye image including a third right-eye object on the right-eye panel region, an operation of scaling at least one of the third left-eye image or the third right-eye image in a first direction or in a second direction orthogonal to the first direction based on an input signal received from an input device, and an operation of generating the size adjustment data based on a scaled size to which the at least one of the third left-eye image or the third right-eye image is scaled.

In example embodiments, the third left-eye object and the third right-eye object may be symmetrical with each other and may have the same size.

In example embodiments, the generating the luminance adjustment data may include deriving the left-eye luminance perception data by displaying a left-eye luminance perception image on the left-eye panel region, and deriving the right-eye luminance perception data by displaying a right-eye luminance perception image on the right-eye panel region. The operation of deriving the left-eye luminance perception data may include an operation of displaying a fourth left-eye image including a fourth left-eye object on the left-eye panel region and a fourth right-eye image on the right-eye panel region, an operation of gradually increasing or decreasing a grayscale of the fourth left-eye object, and an operation of generating the left-eye luminance perception data based on the grayscale of the fourth left-eye object at a time point when an input signal is received from an input device.

In example embodiments, the fourth left-eye image may include a background image having a first grayscale value. The grayscale of the fourth left-eye object may be increased or decreased every predetermined period from the first grayscale value.

In example embodiments, the fourth right-eye image may include a fourth right-eye object including a plurality of rectangular shapes having a plurality of grayscale values.

In example embodiments, the operation of the deriving the right-eye luminance perception data may include an operation of displaying a fifth left-eye image on the left-eye panel region and a fifth right-eye image including a fifth right-eye object on the right-eye panel region, an operation of gradually increasing or decreasing a grayscale of the fifth right-eye object, and an operation of generating the right-eye luminance perception data based on the grayscale of the fifth right-eye object at a time point when the input signal is received.

In example embodiments, the operation of the converting the image source into the input image data may include an operation of adjusting a size of at least one of an input left-eye image or an input right-eye image included in the image source based on the size adjustment data, an operation of adjusting a display starting point of at least one of the input left-eye image or the input right-eye image based on the position adjustment data and the size adjustment data, and an operation of adjusting a luminance of at least one of the input left-eye image or the input right-eye image based on the luminance adjustment data.

According to some example embodiments, a method of driving a head mounted display may include an operation of deriving a binocular disparity adjustment data by displaying a binocular disparity adjustment image on a left-eye panel region and a right-eye panel region, an operation of generating an input image data by adjusting at least one of an input left-eye image displayed on the left-eye panel region or an input right-eye image displayed on the right-eye panel region based on the binocular disparity adjustment data, and an operation of displaying an image corresponding to the input image data on the left-eye panel region and the right-eye panel region.

In example embodiments, the binocular disparity adjustment data may include at least one of a position shift value, a size ratio, or a luminance ratio of a right-eye image with respect to a left-eye image.

In example embodiments, the operation of deriving the binocular disparity adjustment data includes an operation of displaying a binocular balancing image on the left-eye panel region and the right-eye panel region, an operation of deriving a position adjustment data by displaying a binocular position adjustment image on the left-eye panel region and the right-eye panel region, an operation of deriving a size adjustment data by displaying a binocular size adjustment image on the left-eye panel region and the right-eye panel region, an operation of deriving a left-eye luminance perception data by displaying a left-eye luminance perception image on the left-eye panel region, an operation of deriving a right-eye luminance perception data by displaying a right-eye luminance perception image on the right-eye panel region, and an operation of generating a luminance adjustment data based on a difference between the left-eye luminance perception data and the right-eye luminance perception data.

According to some example embodiments, a head mounted display may include a display device configured to display an image on a left-eye panel region and a right-eye panel region, and an image processor configured to derive a binocular disparity adjustment data by providing a binocular disparity adjustment image data to the display device, configured to generate input image data by adjusting at least one of an input left-eye image data for the left-eye panel region or an input right-eye image data for the right-eye panel region based on the binocular disparity adjustment data, and configured to provide the input image data to the display device.

In example embodiments, the binocular disparity adjustment data may include at least one of a position shift value, a size ratio, or a luminance ratio of a right-eye image with respect to a left-eye image.

In example embodiments, the image processor may include an adjustment data determiner configured to determine the binocular disparity adjustment data based on user information and driving information, and an input image generator configured to receive image source and configured to generate the input image data by adjusting at least one of the input left-eye image data or the input right-eye image data included in the image source based on the binocular disparity adjustment data.

Therefore, a method of driving a head mounted display according to example embodiments may derive a binocular disparity adjustment data, may differently adjust the left-eye image and the right-eye image according to the characteristics of user's eyes based on the binocular disparity adjustment data, and may display the adjusted image on a left-eye panel region and a right-eye panel region. Accordingly, it is possible to ensure user accessibility by the universal design and to reduce the fatigue of user.

In addition, a head mounted display according to example embodiments may perform the method to correct the binocular disparity of the user, thereby reducing user's fatigue.

BRIEF DESCRIPTION OF THE DRAWINGS

Exemplary embodiments will be described more fully hereinafter with reference to the accompanying drawings, in which various embodiments are shown.

DESCRIPTION OF EMBODIMENTS

Exemplary embodiments will be described more fully hereinafter with reference to the accompanying drawings, in which various embodiments are shown.

Figure 1:
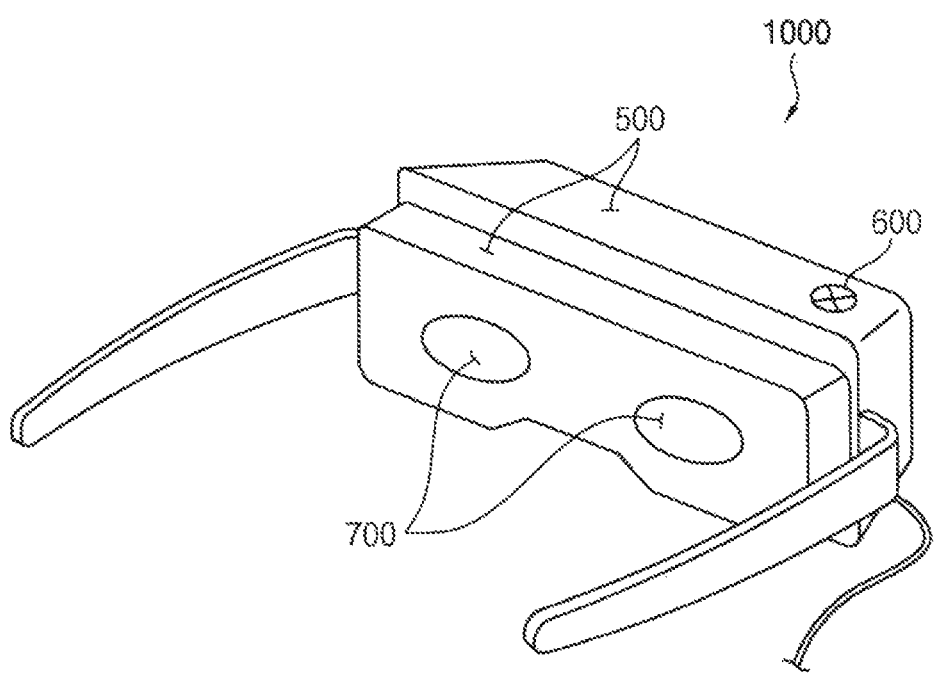
FIGS. 1 and 2 are diagrams illustrating a head mounted display according to example embodiments.
Figure 2:
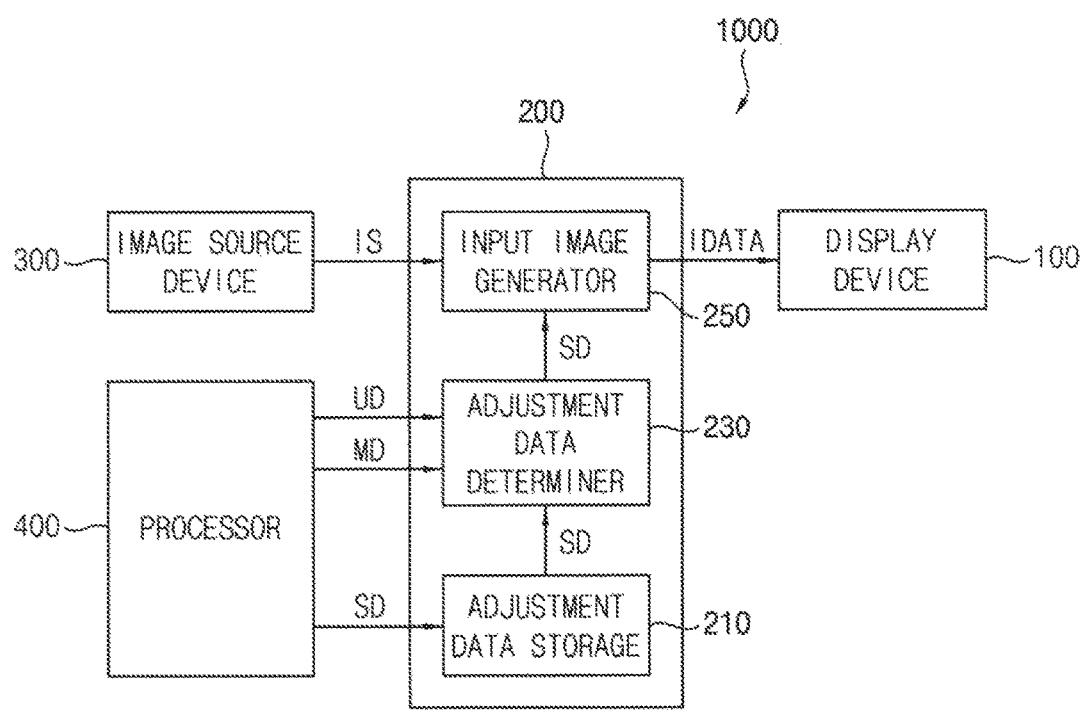

FIGS. 1 and 2 are diagrams illustrating a head mounted display according to example embodiments.

Referring to FIGS. 1 and 2, the head mounted display 1000 may include a display device 100, an image processor 200, an image source device 300, a processor 400, a housing 500, an input device 600, and a lens 700. For example, the display device 100, the image processor 200, the image source device 300, and the processor 400 may be located inside of the housing 500 surrounding them.

The display device 100 may display an image corresponding to the input image data IDATA received from the image processor 200 on a left-eye panel region and a right-eye panel region. For example, the display device 100 may display a left-eye image on the left-eye panel region recognized by the user's left-eye and a right-eye image on the right-eye panel region recognized by the user's right-eye based on the input image data IDATA.

The image processor 200 may provide an image data corresponding to a binocular disparity adjustment image to the display device 100 to perform a binocular disparity test operation for each user and may derive a binocular disparity adjustment data SD. Here, the binocular disparity indicates the difference in the visual perceptions of the user's left-eye and right-eye. The binocular disparity test operation may be for measuring the binocular disparity. The binocular disparity test operation may include a binocular position perception test operation for measuring a difference in position perceptions of both eyes, a binocular size perception test operation for measuring a difference in size perceptions of both eyes, a binocular luminance perception test operation for measuring a difference in luminance perceptions of both eyes, etc. Hereinafter, a method of performing the binocular disparity test operation and deriving the binocular disparity adjustment data SD will be described in more detail with reference to the FIGS. 6 through 19.

The image processor 200 may adjust at least one of an input left-eye image data for the left-eye panel region or an input right-eye image data for the right-eye panel region based on the binocular disparity adjustment data SD. In one example embodiment, the binocular disparity adjustment data SD may include at least one of a position shift value, a size ratio, or a luminance ratio of a right-eye image with respect to a left-eye image. Thus, the image processor 200 may adjust at least one of displaying positions, sizes, or luminances of the input left-eye image data and/or the input right-eye image data based on the binocular disparity adjustment data SD to display the differentially adjusted the left-eye and right-eye images according to the characteristics of user's both eyes on the left-eye panel region and the right-eye panel region. The image processor 200 may generate the input image data IDATA corresponding to adjusted image and may provide the input image data IDATA to the display device 100, thereby differentially driving the left display panel (i.e., the left-eye panel region) and the right display panel (i.e., the right-eye panel region).

In one example embodiment, the image processor 200 may include an adjustment data storage 210, an adjustment data determiner 230, and an input image generator 250.

The adjustment data storage 210 may store the binocular disparity adjustment data SD for each user derived by performing the binocular disparity test operations. For example, the adjustment data storage 210 may include a non-volatile memory device such as an erasable programmable read-only memory (EPROM) device, an electrically erasable programmable read-only memory (EEPROM) device, a flash memory device, a phase change random access memory (PRAM) device, a resistance random access memory (RRAM) device, a nano floating gate memory (NFGM) device, a polymer random access memory (PoRAM) device, a magnetic random access memory (MRAM) device, a ferroelectric random access memory (FRAM) device, etc.

The adjustment data determiner 230 may receive user information UD from the processor and may search the binocular disparity adjustment data SD corresponding to the received user information UD from the adjustment data storage 210. For example, the head mounted display 1000 may sense the biometric information of the user (e.g., iris information, fingerprint information, etc.), and then the adjustment data determiner 230 may receive user information UD corresponding to sensed biometric information to determine the binocular disparity adjustment data SD.

In one example embodiment, the adjustment data determiner 230 may receive driving information MD and may search the binocular disparity adjustment data SD corresponding to the driving information MD from the adjustment data storage 210. For example, the processor 400 in the head mounted display 1000 may provide the driving information MD including a resolution of image source, a driving time, etc. to the adjustment data determiner 230, and then the adjustment data determiner 230 may determine the binocular disparity adjustment data SD corresponding to the resolution of image source or the driving time. For example, when the resolution of image source is relatively high or the driving time exceeds 1 hour, the user can feel the fatigue caused by the correction of binocular disparity. Therefore, the adjustment data determiner 230 may apply a gain value for lowering the degree of correction of binocular disparity to the binocular disparity adjustment data SD.

The input image generator 250 may receive image source IS and may generate the input image data IDATA by adjusting at least one of the input left-eye image data or the input right-eye image data included in the image source IS based on the binocular disparity adjustment data SD.

The image source device 300 may provide the image source IS to the input image generator 250. For example, the image source device 300 may load the image data stored in a storage and may provide the loaded image data to the input image generator 250 of the image processor 200 to display an image on the display device 100.

The processor 400 may provide a variety of information for determining the binocular disparity adjustment data SD to the adjustment data determiner 230. While the binocular disparity adjustment image is displayed, the processor 400 may receive a user input from the input device 600, may generate the binocular disparity adjustment data SD based on the user input, and may store the binocular disparity adjustment data SD in the adjustment data storage 210. In addition, the processor 400 may generate the user information UD corresponding to the biometric information by sensing the biometric information of the user (e.g., iris information, fingerprint information, etc.) and may generate the driving information MD including the resolution of image source, the driving time, etc.

The input device 600 may receive a user input while the binocular disparity test operation is performed. For example, the input device 600 may directly receive the user input via a wired manner (e.g., using a physical button) or indirectly receive the user input via a wireless manner (e.g., using a remote controller).

In addition, the head mounted display 1000 may further include a housing 500 for protecting the display device 100 and the lens 700 in the housing 500. The head mounted display 1000 may further include lens, reflectors, optical elements, and the like for forming or adjusting an optical path in order that an image displayed on the display device 100 is provided to the user's eyes.

Figure 3:
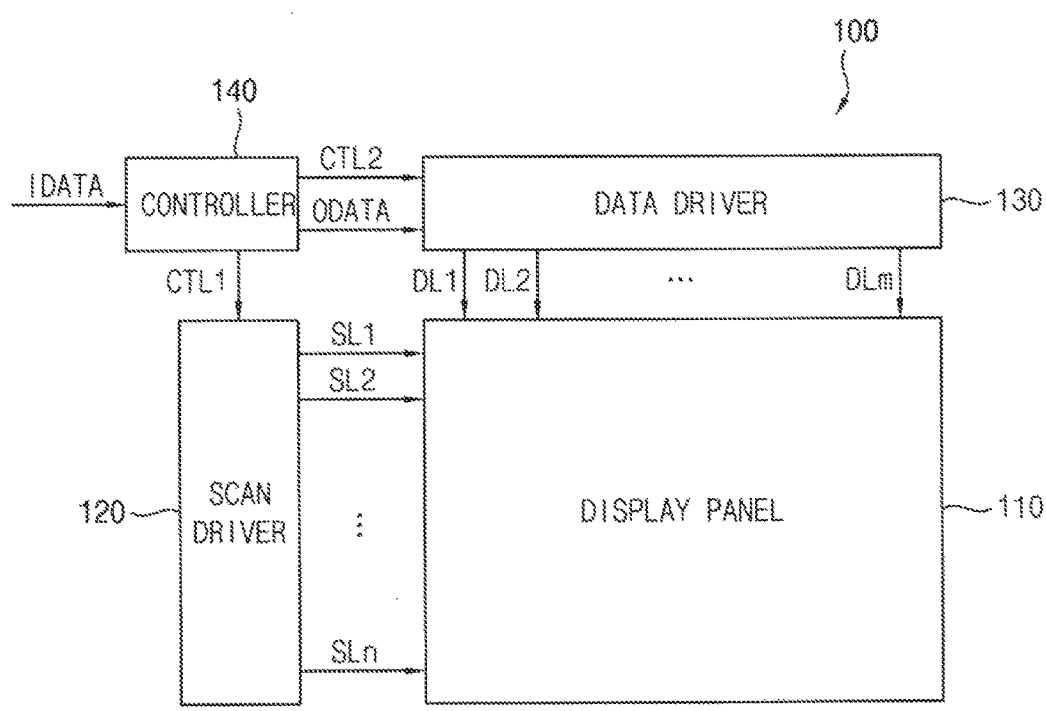
FIG. 3 is a block diagram illustrating an example of a display device included in a head mounted display of FIG. 1.
Figure 4:
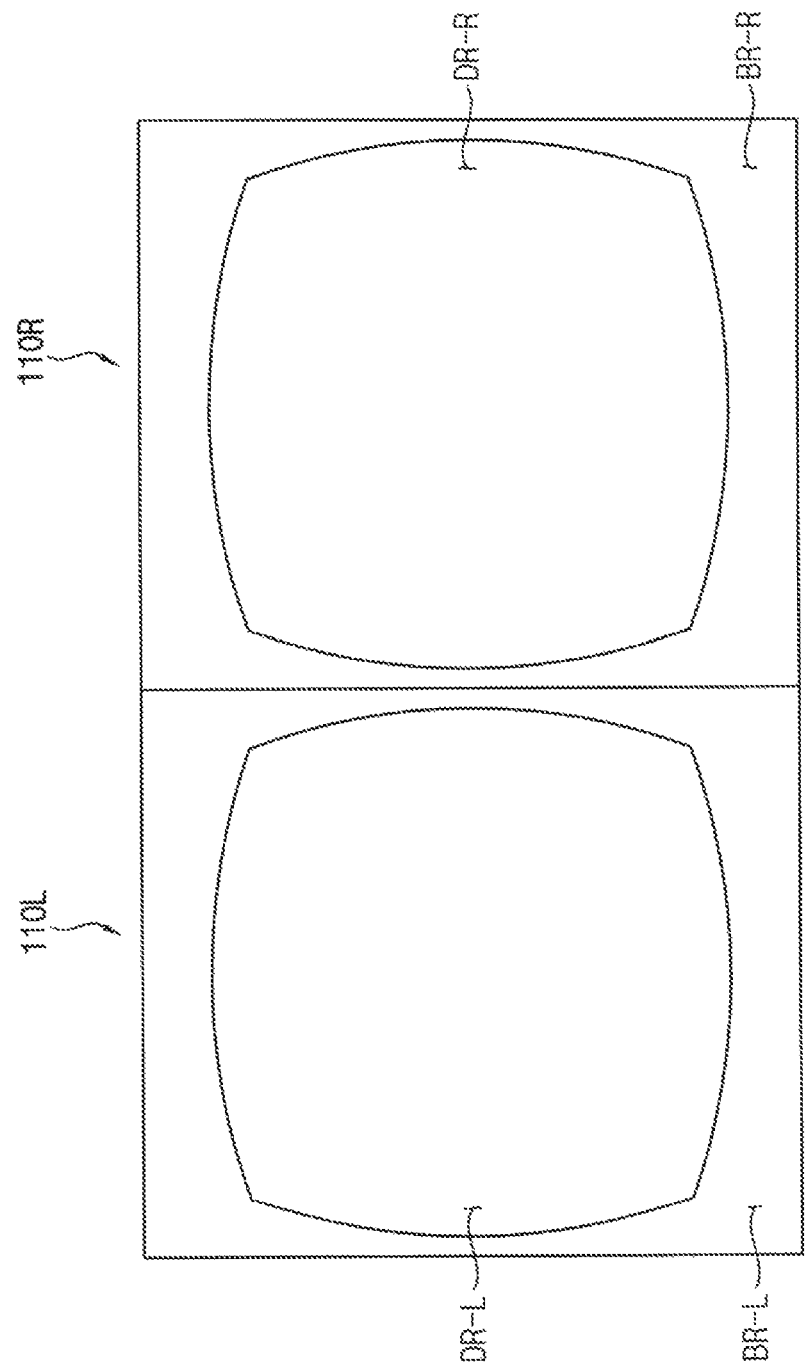
FIG. 4 is a diagram illustrating an example of a display panel included in a display device of FIG. 3.

FIG. 3 is a block diagram illustrating an example of a display device included in a head mounted display of FIG. 1. FIG. 4 is a diagram illustrating an example of a display panel included in a display device of FIG. 3.

Referring to FIGS. 3 and 4, the display device 100 may include a display panel 110 and a panel driver. The panel driver may include a scan driver 120, a data driver 130, and a controller 140.

The display panel 110 may include a left-eye panel region 110L and a right-eye panel region 110R each including a plurality of pixels. For example, as shown in FIG. 4, the left-eye panel region 110L may include a first left-eye display region DR-L on which a left-eye image is displayed and a second left-eye display region BR-L on which a black image is displayed. The left-eye image may be recognized by user's left-eye. The second left-eye display region BR-L may be located outside of the first left-eye display region DR-L to surround the first left-eye display region DR-L. The right-eye panel region 110R may include a first right-eye display region DR-R on which a right-eye image is displayed and a second right-eye display region BR-R on which a black image is displayed. The right-eye image may be recognized by user's right-eye. The second right-eye display region BR-R may be located outside of the first right-eye display region DR-R to surround the first right-eye display region DR-R.

The scan driver 120 may provide scan signals to the pixels via the scan lines SL1 through SLn based on a first control signal CTL1.

The data driver 130 may receive a second control signal CTL2 and output image data ODATA. The data driver 130 may convert the output image data ODATA into analog type data signals, and then may provide the converted data signals to the pixels via the data lines DL1 through DLm based on the second control signal CTL2.

The controller 140 may control the scan driver 120 and the data driver 130 to display an image corresponding to input image data IDATA. The controller 140 may receive input image data IDATA from the image processor 400. The controller 140 may generate first and second control signals CTL1 and CTL2 to control the scan driver 120 and the data driver 130, respectively. For example, the first control signal CTL1 for controlling the scan driver 120 may include a vertical start signal, a scan clock signal, etc. The second control signal CTL2 for controlling the data driver 130 may include a horizontal start signal, a load signal, etc. The controller 140 may generate digital type output image data ODATA compatible to the operation condition of the display panel 110 based on the input image data IDATA, and then provide the output image data ODATA to the data driver 130.

Although the example embodiments of FIGS. 3 and 4 describe that the left-eye panel region 110L and the right-eye panel region 110R are driven by the same scan driver and the same data driver, it is not limited thereto. For example, the display device may include a first scan driver and a first data driver for driving the left-eye panel region 110L, and a second scan driver and a second data driver for driving the right-eye panel region 110R.

Although the example embodiments of FIGS. 3 and 4 describe that the display device 100 includes single display panel 110 having a left-eye panel region 110L and a right-eye panel region 110R, a structure of the display panel is not limited thereto. For example, the display device 100 includes a first display panel having a left-eye panel region and a second display panel having a right-eye panel region.

Figure 5A:
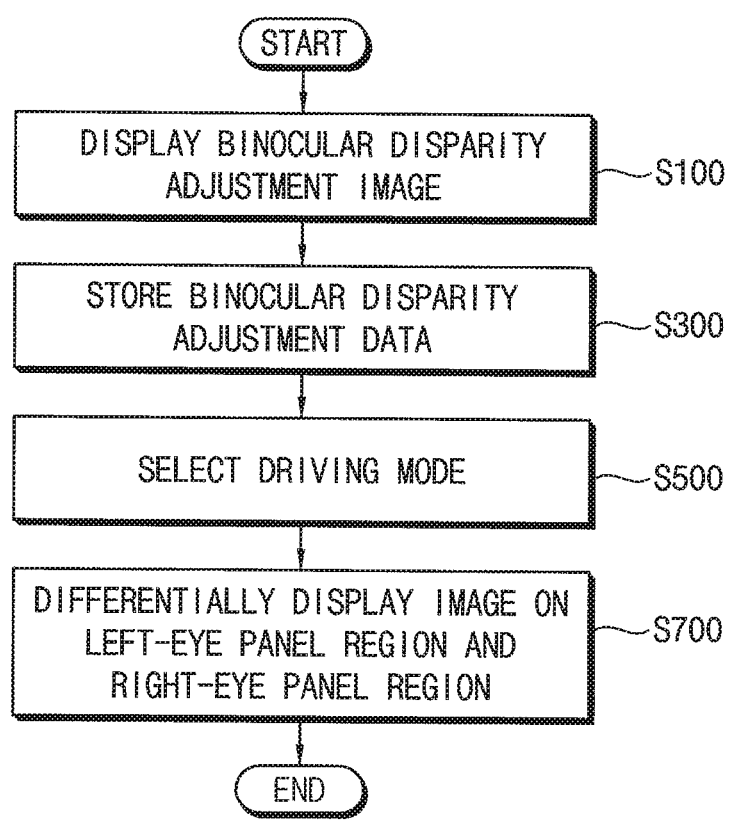
FIGS. 5A and 5B are flow charts illustrating a method of driving a head mounted display according to one example embodiment.
Figure 5B:
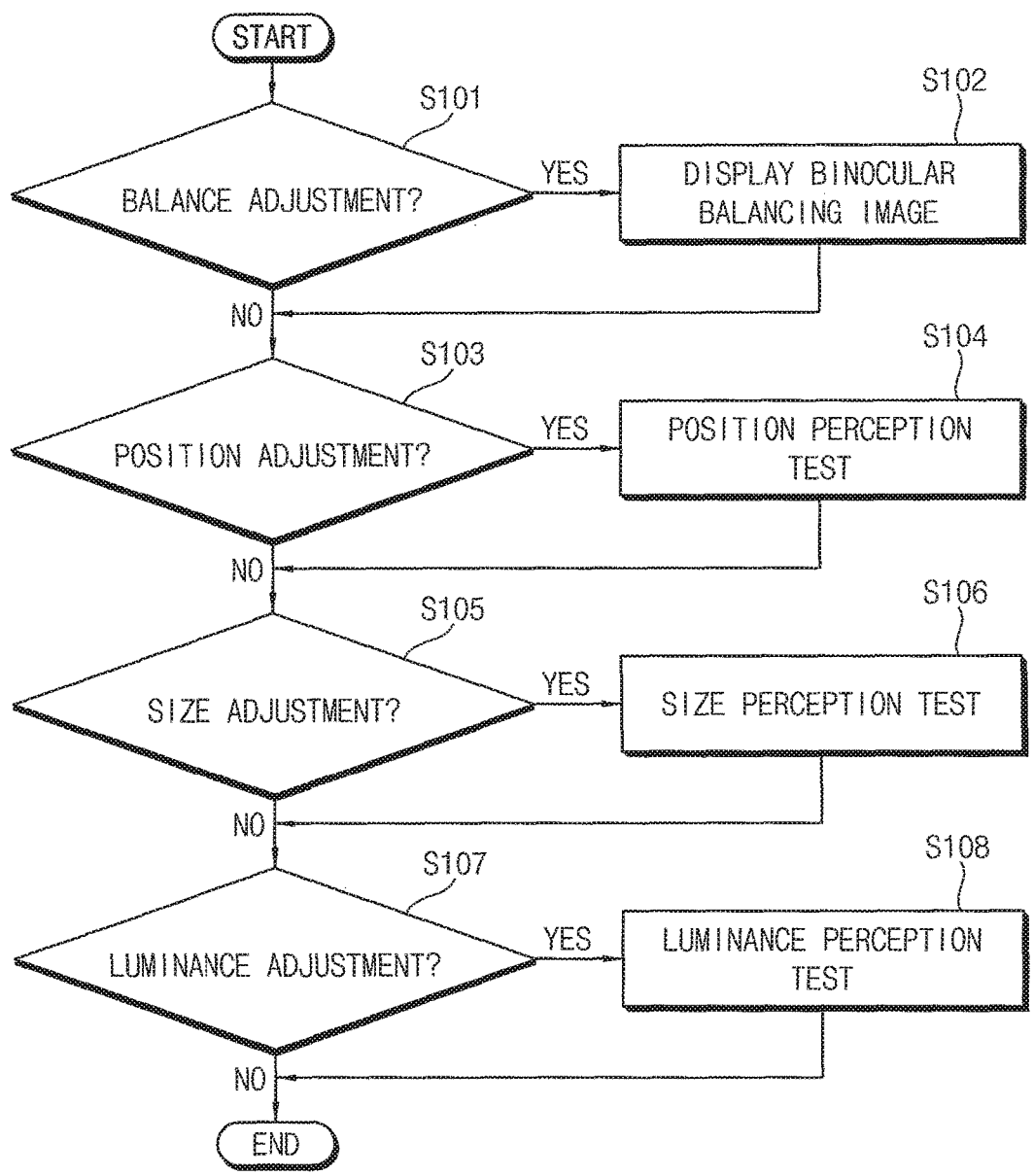

FIGS. 5A and 5B are flow charts illustrating a method of driving a head mounted display according to one example embodiment.

Referring to FIGS. 5A and 5B, the method of driving the head mounted display is provided. The method may display a binocular disparity adjustment image on a left-eye panel region and a right-eye panel region (S100) and may derive a binocular disparity adjustment data SD. The binocular disparity adjustment data SD may include at least one of a position shift value, a size ratio, or a luminance ratio of a right-eye image with respect to a left-eye image.

As shown in FIG. 5B, at least one of the position shift value for adjusting position deviation, the size ratio for adjusting size deviation, or the luminance ratio for adjusting luminance deviation may be derived as the binocular disparity adjustment data SD by displaying the binocular disparity adjustment image. In one example embodiment, when it is required to adjust binocular balance (S101), a binocular balancing image may be displayed on the left-eye panel region and the right-eye panel region (S102). When it is required to adjust binocular position deviation (S103), the binocular position perception test operation for adjusting the position of the right-eye with respect to the left-eye may be performed (S104). For example, a position adjustment data may be derived by displaying a binocular position adjustment image on the left-eye panel region and the right-eye panel region. When it is required to adjust binocular size deviation (S105), the binocular size perception test operation for adjusting the size ratio of the right-eye image with respect to the left-eye image in the first direction and/or the second direction may be performed (S106). For example, a size adjustment data may be derived by displaying a binocular size adjustment image on the left-eye panel region and the right-eye panel region. When it is required to adjust binocular luminance deviation (S107), the binocular luminance perception test operation for adjusting the luminance ratio of the right-eye image with respect to the left-eye image may be performed (S108). For example, a left-eye luminance perception data may be derived by displaying a left-eye luminance perception image on the left-eye panel region. A right-eye luminance perception data may be derived by displaying a right-eye luminance perception image on the right-eye panel region. A luminance adjustment data may be generated based on a difference between the left-eye luminance perception data and the right-eye luminance perception data.

The derived binocular disparity adjustment data SD may be stored in an adjustment data storage (S300). For example, the binocular disparity adjustment data SD for each of the registered users of the head mounted display may be stored in the adjustment data storage with user information. Because the binocular disparities for registered users are different from each other, the binocular disparity adjustment data SD for each user may be derived respectively and the binocular disparity for each user can be corrected.

The driving mode related to the degree of correction of the binocular disparity may be selected (S500). If the user has binocular vision dysfunction, it may give a strain on the user's eyes because the head mounted display displays the corrected image of the binocular disparity for a long time. Therefore, it is possible to determine whether or not to correct the binocular disparity or to select the driving mode to vary the degree of correction based on a user's input or the driving information (e.g., the resolution of the image source, the driving time, etc.).

The image may be differentially displayed on the left-eye panel region and the right-eye panel region based on the binocular disparity adjustment data SD (S700). Thus, the image processor may determine the binocular disparity adjustment data SD based on the user information and the selected driving mode, and may generate input image data by adjusting at least one of input left-eye image data or input right-eye image data based on the determined binocular disparity adjustment data SD. In addition, the display device may display the left-eye image and the right-eye image corresponding to the input image data on the left-eye panel region and the right-eye panel region, respectively. Hereinafter, a method of differentially displaying the image on the left-eye panel region and the right-eye panel region based on the binocular disparity adjustment data SD will be described in more detail with reference to the FIG. 20.

Figure 6:
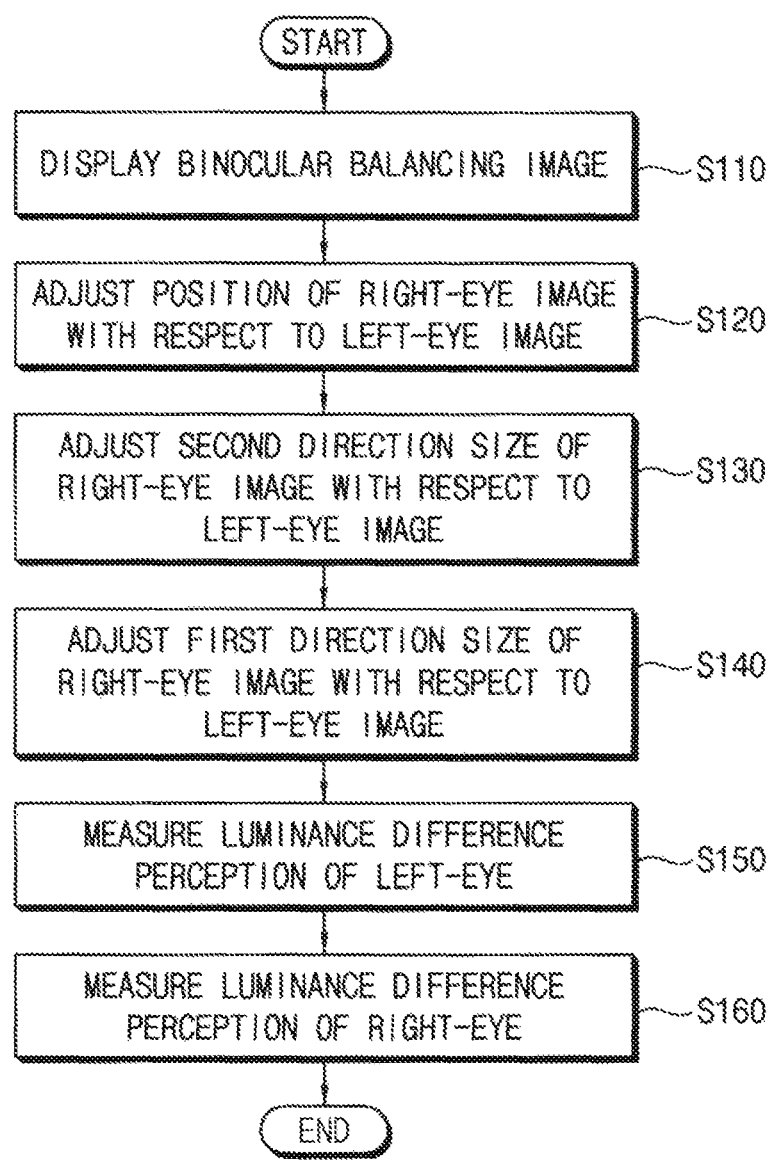
FIG. 6 is a flow chart illustrating one example of a method of deriving a binocular disparity adjustment data in a method of driving a head mounted display of FIGS. 5A and 5B.
Figure 7:
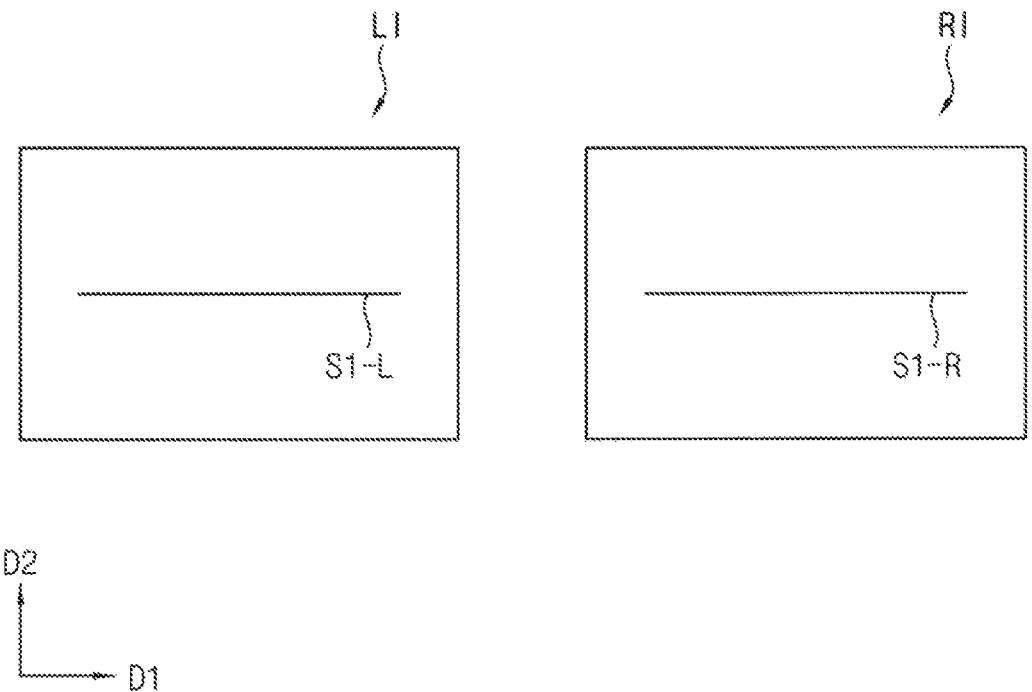
FIG. 7 is a diagram illustrating an example of a binocular balancing image displayed on a display panel.
Figure 8A:
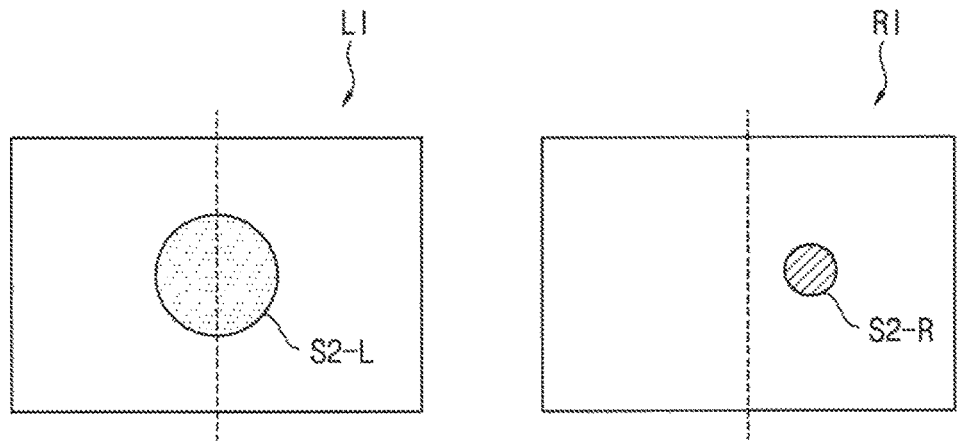
FIGS. 8A and 8B are diagrams illustrating an example of a binocular position adjustment image displayed on a display panel.
Figure 8A:
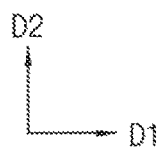
Figure 8B:
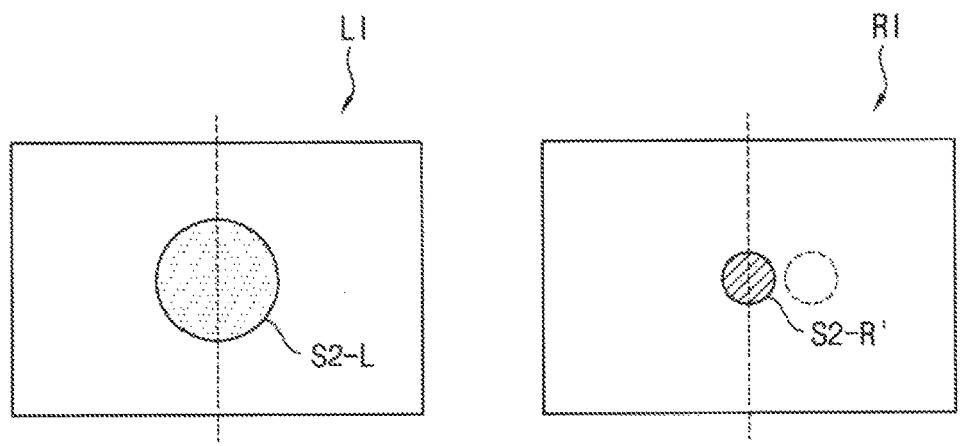
Figure 8B:
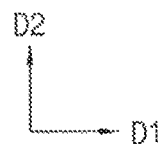
Figure 9A:
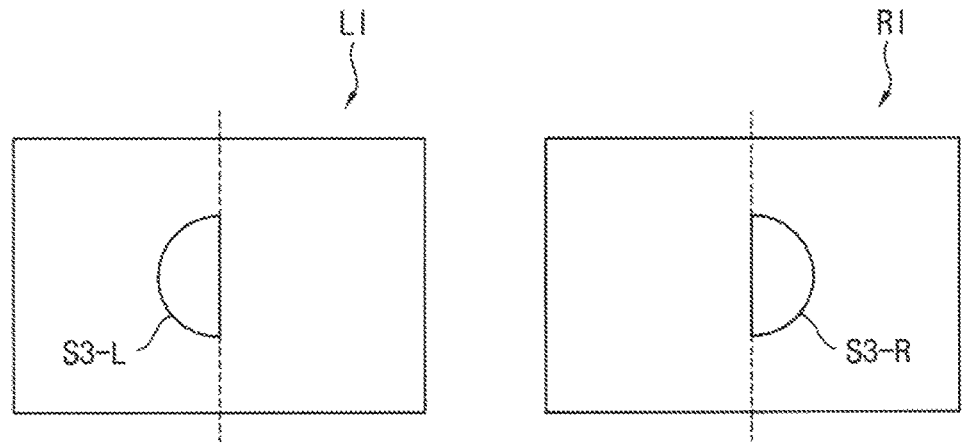
FIGS. 9A and 9B are diagrams illustrating one example of a binocular size adjustment image displayed on a display panel.
Figure 9B:
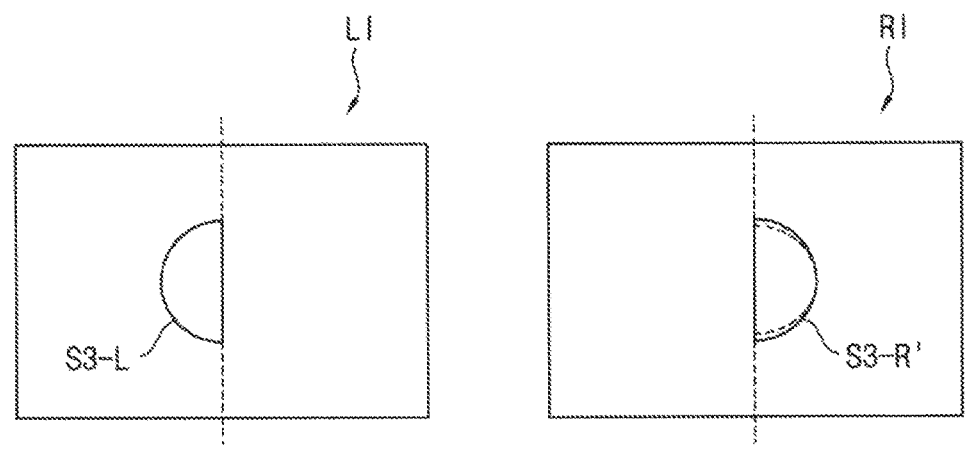
Figure 10A:
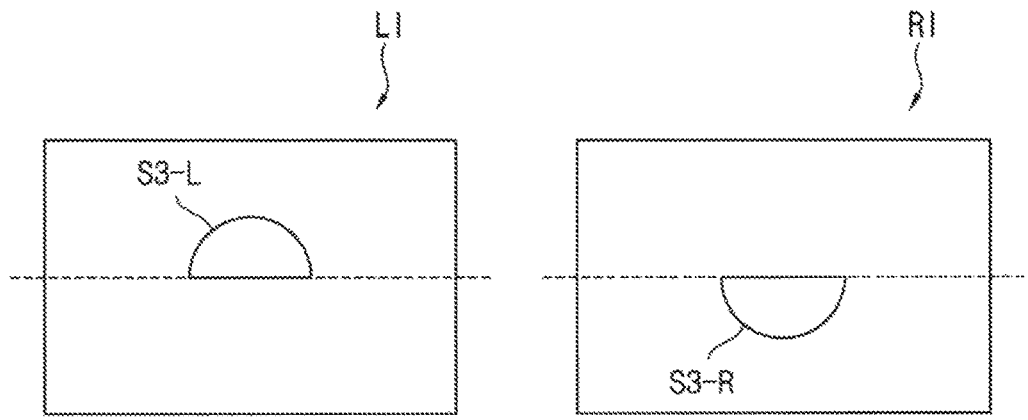
FIGS. 10A and 10B are diagrams illustrating another example of a binocular size adjustment image displayed on a display panel.
Figure 10B:
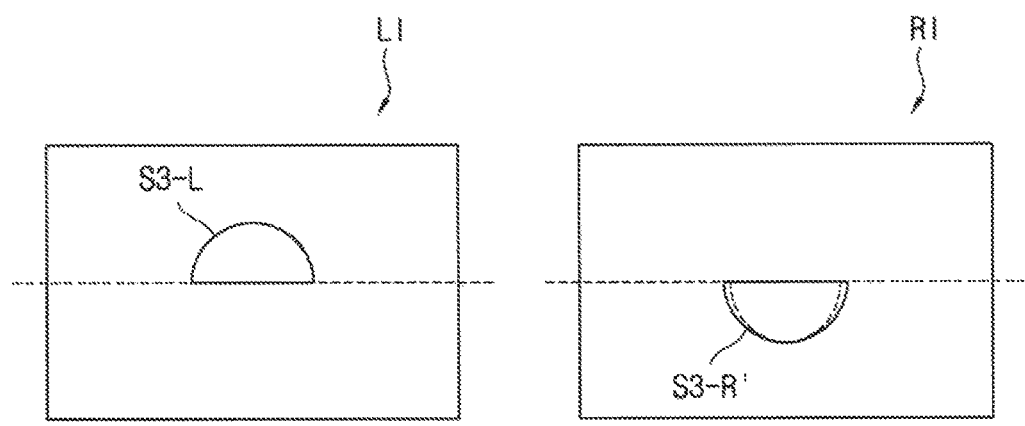
Figure 11:
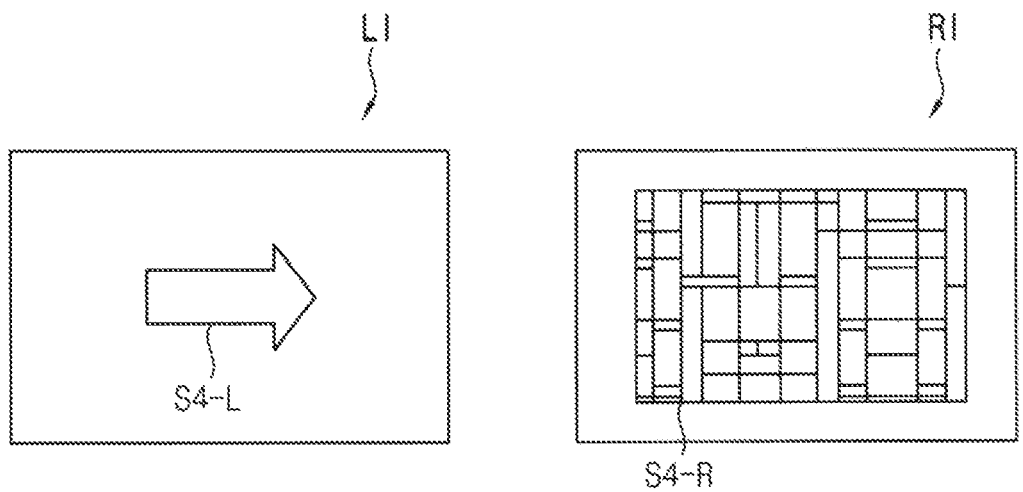
FIG. 11 is a diagram illustrating an example of a left-eye luminance perception image displayed on a display panel.
Figure 12:
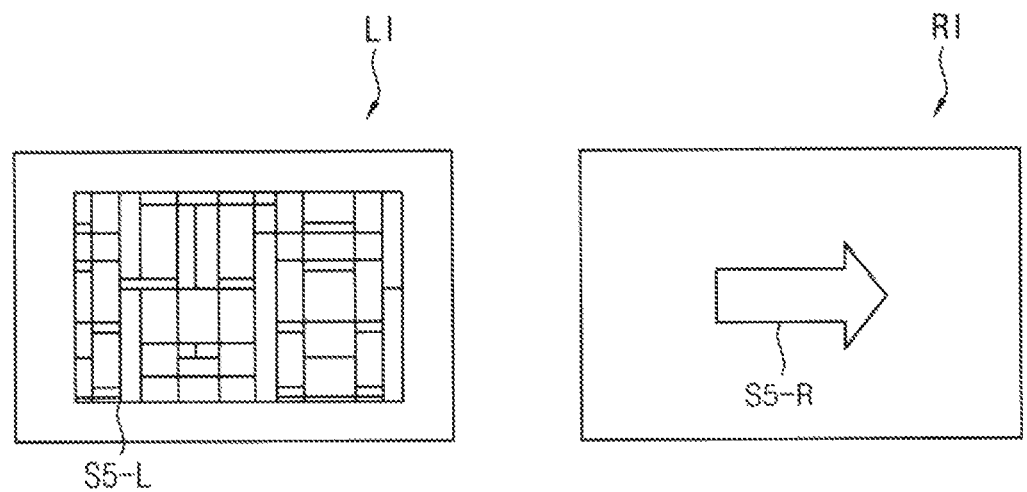
FIG. 12 is a diagram illustrating an example of a right-eye luminance perception image displayed on a display panel.

FIG. 6 is a flow chart illustrating one example of a method of deriving a binocular disparity adjustment data SD in a method of driving a head mounted display of FIGS. 5A and 5B. FIG. 7 is a diagram illustrating an example of a binocular balancing image displayed on a display panel. FIGS. 8A and 8B are diagrams illustrating an example of a binocular position adjustment image displayed on a display panel. FIGS. 9A and 9B are diagrams illustrating one example of a binocular size adjustment image displayed on a display panel. FIGS. 10A and 10B are diagrams illustrating another example of a binocular size adjustment image displayed on a display panel. FIG. 11 is a diagram illustrating an example of a left-eye luminance perception image displayed on a display panel. FIG. 12 is a diagram illustrating an example of a right-eye luminance perception image displayed on a display panel.

Referring to FIGS. 6 through 12, the binocular disparity adjustment data SD may be derived by performing the binocular disparity test operations (e.g., a binocular position perception test operation, a binocular size perception test operation, and a binocular luminance perception test operation).

A binocular balancing image may be displayed on the left-eye panel region and the right-eye panel region (S110). Even in the case of the same user, the binocular disparity may be measured differently depending on the wearing state of the head mounted display. Therefore, in order to accurately perform the binocular disparity test operations, the head mounted display may display the binocular balancing image on the left-eye panel region and the right-eye panel region, and the user may adjust the wearing state on the basis of the binocular balancing image.

As shown in FIG. 7, the head mounted display may display a left-eye image LI on the left-eye panel region and a right-eye image RI on the right-eye panel region as the binocular balancing image. The left-eye image LI may include a first left-eye object S1-L. The right-eye image RI may include a first right-eye object S1-R. The first left-eye object S1-L and the first right-eye object S1-R may have substantially the same shapes. For example, the first left-eye object S1-L and the first right-eye object S1-R may be straight lines extending in the first direction D1 (i.e., the horizontal direction). Accordingly, the user may adjust the wearing state of the head mounted display such that the first left-eye object S1-L and the first right-eye object S1-R overlap each other to be in a single line.

The binocular position perception test operation for adjusting the position of the right-eye with respect to the left-eye may be performed (S120). For example, because the difference in position between the left-eye and the right-eye may be relatively largely perceived by the user having strabismus, it is necessary to adjust positions of the left-eye image and the right-eye image. A position adjustment data may be derived by displaying the binocular position adjustment image on the left-eye panel region and the right-eye panel region.

As shown in FIG. 8A, to perform the binocular position perception test operation, the head mounted display may display a left-eye image LI including a second left-eye object S2-L on the left-eye panel region and a right-eye image RI including a second right-eye object S2-R on the right-eye panel region. In one example embodiment, the second left-eye object S2-L and the second right-eye object S2-R may have different sizes and have substantially the same shape. In one example embodiment, a first color of the second left-eye object S2-L may be complementary to a second color of the second right-eye object S2-R. For example, the second left-eye object S2-L may be a red color circle having a visual angle of about 5 to about 10 degrees and may be disposed on the center of the left-eye image LI. The second right-eye object S2-R may be a cyan color circle having a visual angle of about 1 degree and may be disposed on the center of the right eye image RI or deviated from the center of the right eye image RI and disposed on the right side of the center, for example.

As shown in FIG. 8B, the user may move the right-eye image RI in a first direction D1 using an input device 600. The x-axis value of the position of the right-eye image RI corresponding to the first direction D1 may be increased or decreased using the input device 600 to place the moved second right-eye object S2-R' at the center of the second left-eye object S2-L. The position adjustment data can be generated based on a distance and a direction that the right-eye image RI has been moved in the first direction D1. When the first color of the second left-eye object S2-L and the second color of the second right-eye object S2-R' are complementary to each other, the second right-eye object S2-R' can be more clearly distinguished from the second left-eye object S2-L, and then the position adjustment data can be derived more accurately.

Although the example embodiments of FIGS. 8A and 8B describe that the second left-eye object S2-L and the second right-eye object S2-R have the circle shapes, the second left-eye object S2-L and the second right-eye object S2-R may have a variety of shapes such as a linear shape, an arrow shape, a cross shape, a composite shape composed of various shapes, etc.

A binocular size perception test operation may be performed to adjust the size ratio of the right-eye image with respect to the left-eye image in the second direction (S130). For example, if the user has a binocular vision dysfunction (e.g., aniseikonia), the difference in viewing size between the left-eye and the right-eye can be largely perceived. Therefore, it needs to adjust the sizes of the left-eye image and the right-eye image. Accordingly, a size adjustment data may be derived by displaying a binocular size adjustment image on the left-eye panel region and the right-eye panel region.

As shown in FIG. 9A, in the binocular size perception test operation, the head mounted display may display a left-eye image LI including a third left-eye object S3-L on the left-eye panel region and a right-eye image RI including a third right-eye object S3-R on the right-eye panel region. In one example embodiment, the third left-eye object S3-L and the third right-eye object S3-R may be symmetrical with each other and may have the same size. For example, in order to adjust the size with respect to the second direction D2, the third left-eye object S3-L may be a left semicircle of a circle having a visual angle of about 5 to about 10 degrees and may be disposed on the left side of the center of the left-eye image LI. The third right-eye object S3-R may be a right semicircle of the circle having the visual angle of about 5 to about 10 degrees and may be disposed on the right side of the center of the right-eye image RI. The third left-eye object S3-L and the third right-eye object S3-R may have achromatic color and may have brightness different from brightness of a background image.

As shown in FIG. 9B, the user may scale a size of the right-eye image RI in y-axis corresponding to a second direction D2 using an input device such that the scaled third right-eye object S3-R' and the third left-eye object S3-L are recognized as a single circle. The size adjustment data may be generated based on a scaled size (or up-scaling ratio) to which the third right-eye image RI is scaled in the second direction D2.

A binocular size perception test operation may be performed to adjust the size ratio of the right-eye image with respect to the left-eye image in the first direction (S140).

As shown in FIG. 10A, in the binocular size perception test operation, the third left-eye object S3-L may be an upper semicircle of a circle having a visual angle of about 5 to about 10 degrees and may be disposed on the upper side of the center of the left-eye image LI. The third right-eye object S3-R may be a lower semicircle of the circle having the visual angle of about 5 to about 10 degrees and may be disposed on the lower side of the center of the right-eye image RI.

As shown in FIG. 10B, the user may scale a size of the right-eye image RI in x-axis corresponding to a first direction D1 using the input device such that the scaled third right-eye object S3-R' and the third left-eye object S3-L are recognized as a single circle. The size adjustment data may be generated based on the scaled size (or up-scaling ratio) to which the third right-eye image RI is scaled in the first direction D1.

A left-eye luminance perception test operation for measuring a luminance difference perception degree of the left-eye may be performed (S150), and then a right-eye luminance perception test operation for measuring a luminance difference perception degree of the right-eye may be performed (S160). For example, because the difference in luminance between the left-eye and the right-eye may be relatively largely perceived by the user having amblyopia or anisometropia, it is necessary to adjust luminances of the left-eye image and the right-eye image. Therefore, a left-eye luminance perception data may be derived by displaying a left-eye luminance perception image on the left-eye panel region. A right-eye luminance perception data may be derived by displaying a right-eye luminance perception image on the right-eye panel region. And then a luminance adjustment data may be generated based on a difference between the left-eye luminance perception data and the right-eye luminance perception data.

As shown in FIG. 11, in the left-eye luminance perception test operation, the head mounted display may display a left-eye image LI including a fourth left-eye object S4-L on the left-eye panel region and a right-eye image RI including a fourth right-eye object S4-R on the right-eye panel region to derive the left-eye luminance perception data. The left-eye image LI may further include a background image having a first grayscale value, and the grayscale of the fourth left-eye object S4-L may be increased or decreased every predetermined period from the first grayscale value. In addition, the fourth right-eye object S4-R may include a plurality of achromatic rectangles having a plurality of grayscale values to accurately derive the left-eye luminance perception data by dispersing the user's concentration. For example, the background image of the left-eye image LI may have 250 grayscale, the fourth left-eye object S4-L may have an arrow shape having a visual angle of about 5 to about 10 degrees, and then the grayscale of the fourth left-eye object S4-L may be decreased by 1 grayscale every 500 ms from 250 grayscale that is the same as the grayscale of the background image. The user inputs to the input device when the fourth left-eye object S4-L having the arrow shape is recognized by the user. The left-eye luminance perception data may be generated based on the grayscale of the fourth left-eye object S4-L at a time point when an input signal is received from an input device. For example, if the user recognize the fourth left-eye object S4-L when the grayscale of the fourth left-eye object S4-L corresponding to the second grayscale value (e.g., 220 grayscale), a difference between the first grayscale and the second grayscale (e.g., 250 grayscale−220 grayscale=30) may be set as the left-eye luminance perception data.

As shown in FIG. 12, in the right-eye luminance perception test operation, the head mounted display may display a left-eye image LI including a fifth left-eye object S5-L on the left-eye panel region and a right-eye image RI including a fifth right-eye object S5-R on the right-eye panel region to derive the right-eye luminance perception data. The right-eye image RI may further include a background image having a first grayscale value, and the grayscale of the fifth right-eye object S5-R may be increased or decreased every predetermined period from the first grayscale value. In addition, the fifth left-eye object S5-L may include a plurality of achromatic rectangles having a plurality of grayscale values to accurately derive the right-eye luminance perception data by dispersing the user's concentration. For example, the background image of the right-eye image RI may have 250 grayscale, the fifth right-eye object S5-R may have an arrow shape having a visual angle of about 5 to about 10 degrees, and then the grayscale of the fifth right-eye object S5-R may be decreased by 1 grayscale every 500 ms from 250 grayscale that is the same as the grayscale of the background image. The user inputs to the input device when the fifth right-eye object S5-R having the arrow shape is recognized by the user. The right-eye luminance perception data may be generated based on the grayscale of the fifth right-eye object S5-R at a time point when the input signal is received from the input device. For example, if the user recognize the fifth right-eye object S5-R when the grayscale of the fifth right-eye object S5-R corresponding to the third grayscale value (e.g., 235 grayscale), a difference between the first grayscale and the third grayscale (e.g., 250 grayscale−235 grayscale=15) may be set as the right-eye luminance perception data. Accordingly, the luminance adjustment data may be set to a difference between the left-eye luminance perception data and the right-eye luminance perception data (e.g., 30−15=15).

Therefore, the binocular disparity test operations such as a binocular position perception test operation, a binocular size perception test operation, and a binocular luminance perception test operation are performed, and then the position adjustment data, the size adjustment data, and the luminance adjustment data are derived to differentially drive the left-eye panel region and the right-eye panel region according to the characteristics of user's eyes.

Although the example embodiments of FIGS. 11 and 12 describe that the grayscale of the fourth left-eye object S4-L or the grayscale of the fifth right-eye object S5-R is gradually decreased, the grayscale of the fourth left-eye object S4-L or the grayscale of the fifth right-eye object S5-R can be gradually increased from a background image having zero gray scale.

Although the example embodiments of FIG. 6 describe that binocular position perception test operation, the binocular size perception test operations, and the luminance perception test operations are performed sequentially, procedure of the test operations is not limited thereto. For example, the test operations may be performed selectively, and the order of the test operations may be determined in various ways.

Figure 13:
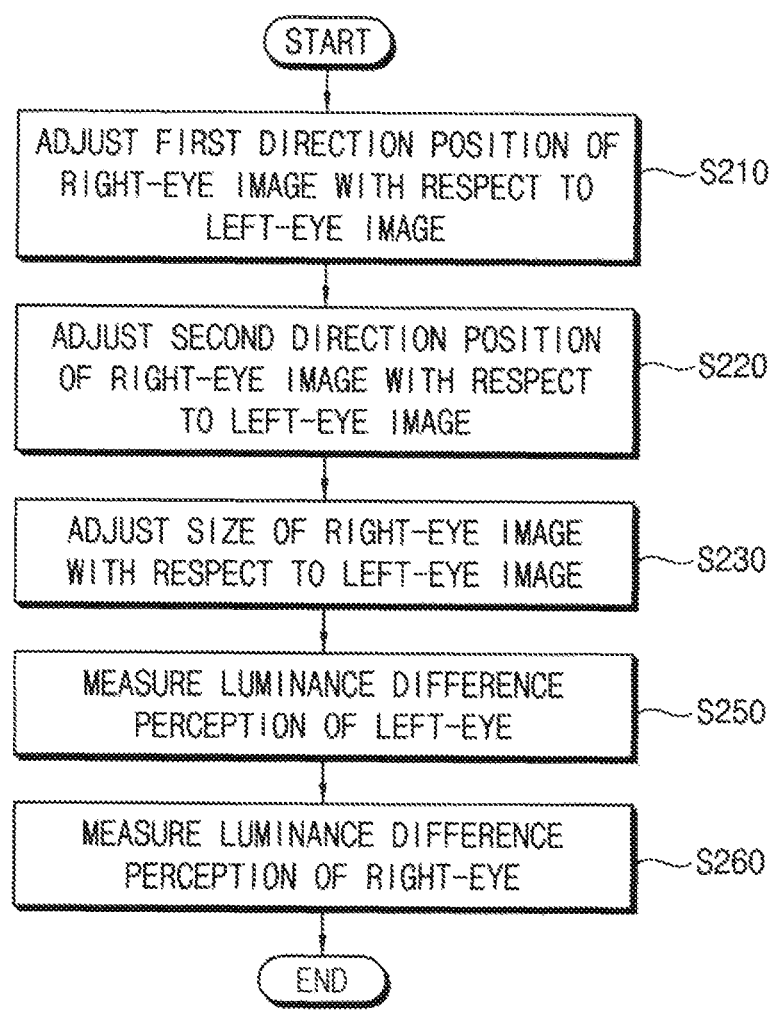
FIG. 13 is a flow chart illustrating another example of a method of deriving a binocular disparity adjustment data in a method of driving a head mounted display of FIGS. 5A and 5B.
Figure 14A:
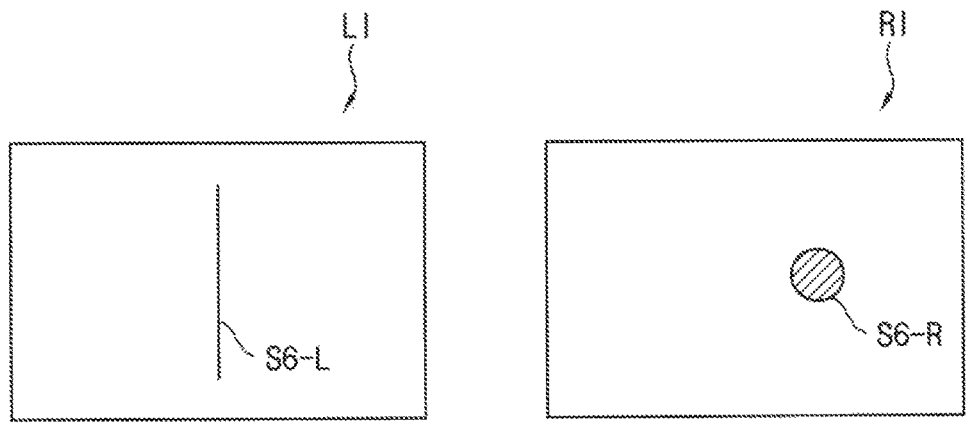
FIGS. 14A and 14B are diagrams illustrating one example of a binocular position adjustment image displayed on a display panel.
Figure 14A:
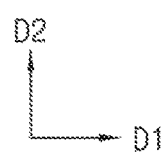
Figure 14B:
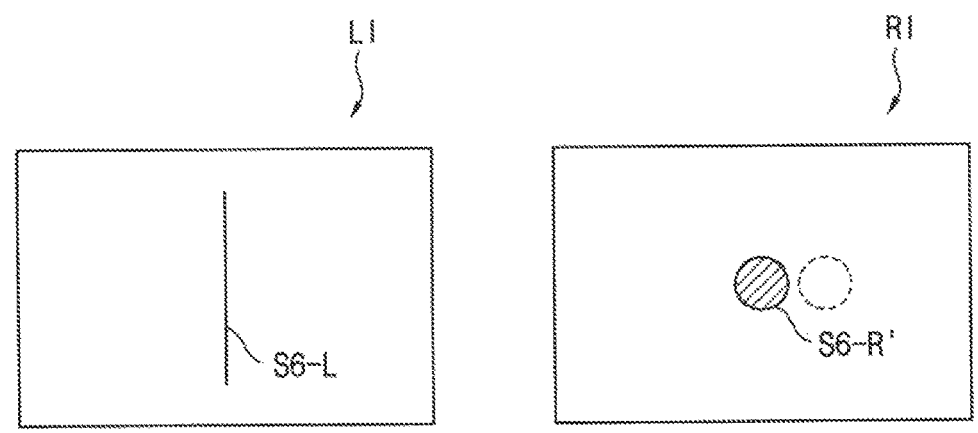
Figure 14B:
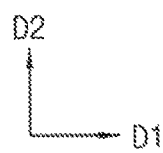
Figure 15A:
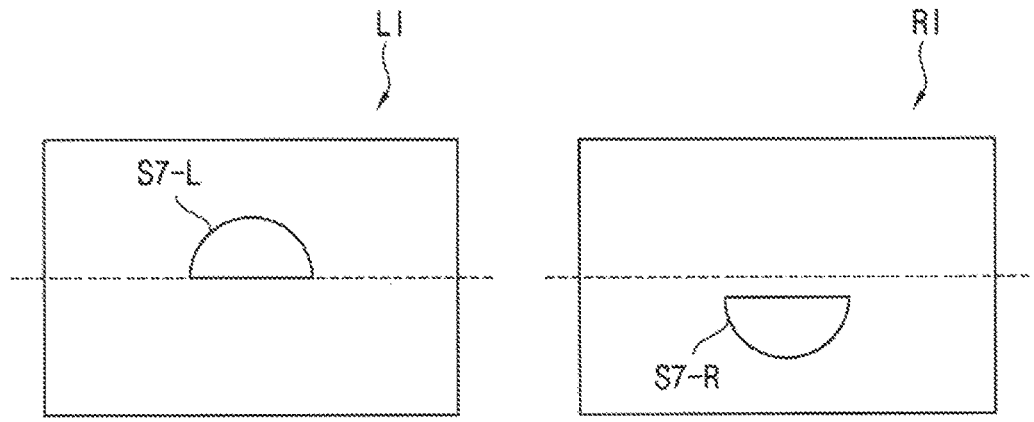
FIGS. 15A and 15B are diagrams illustrating another example of a binocular position adjustment image displayed on a display panel.
Figure 15B:
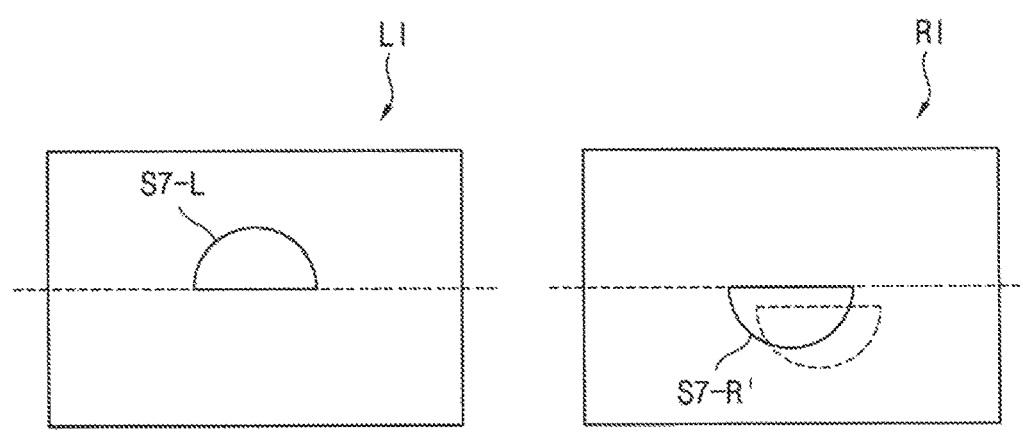
Figure 16A:
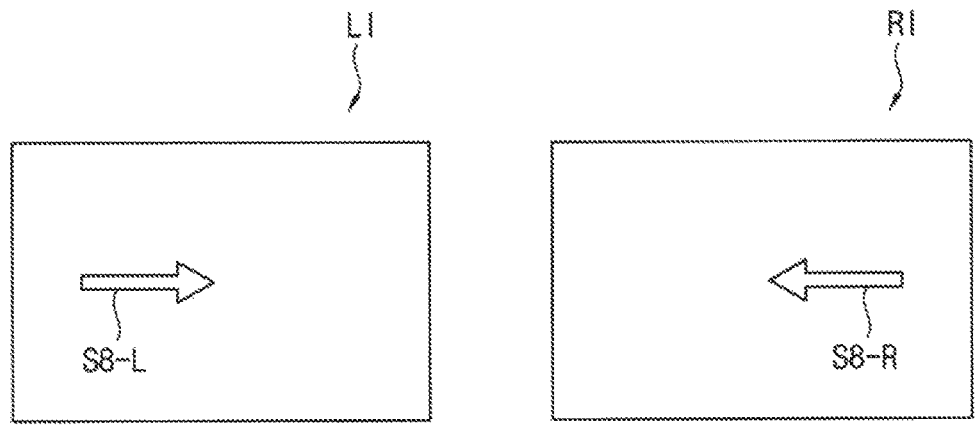
FIGS. 16A and 16B are diagrams illustrating still another example of a binocular position adjustment image displayed on a display panel.
Figure 16A:
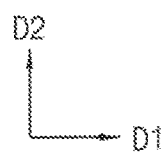
Figure 16B:
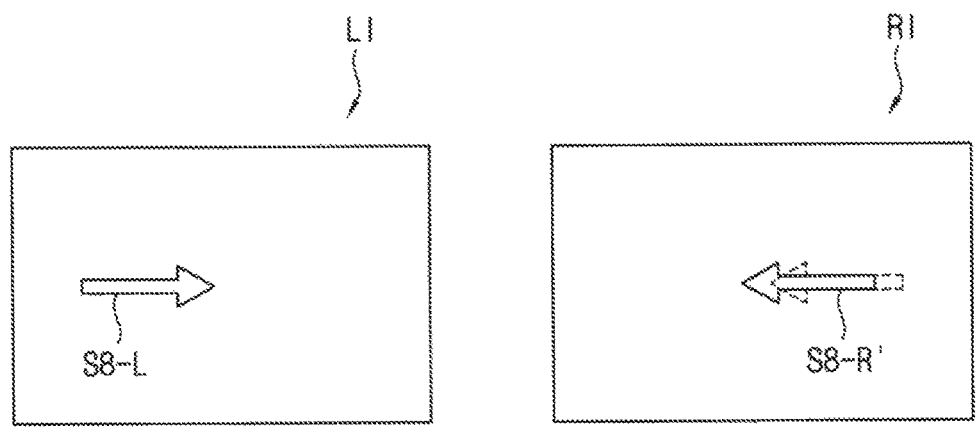
Figure 16B:
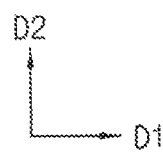
Figure 17A:
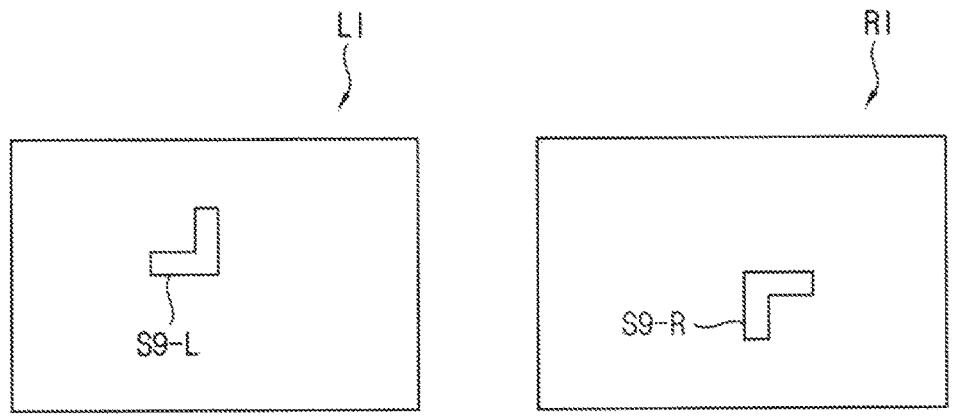
FIGS. 17A and 17B are diagrams illustrating still another example of a binocular position adjustment image displayed on a display panel.
Figure 17B:
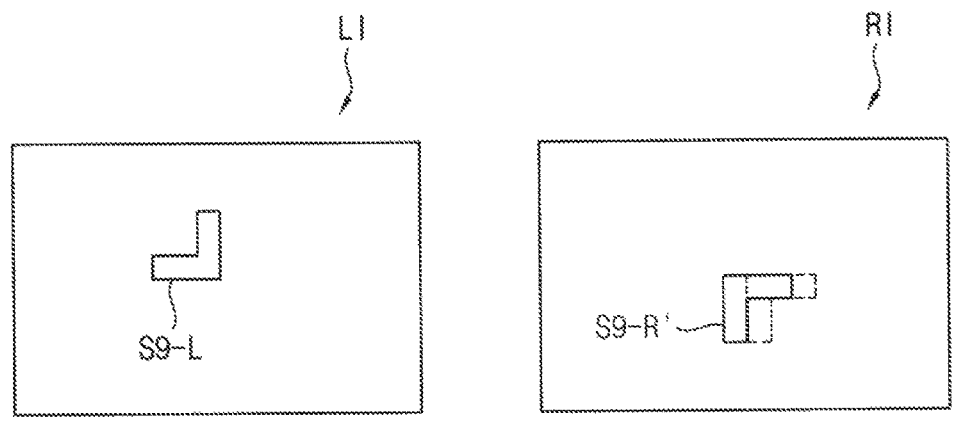
Figure 18:
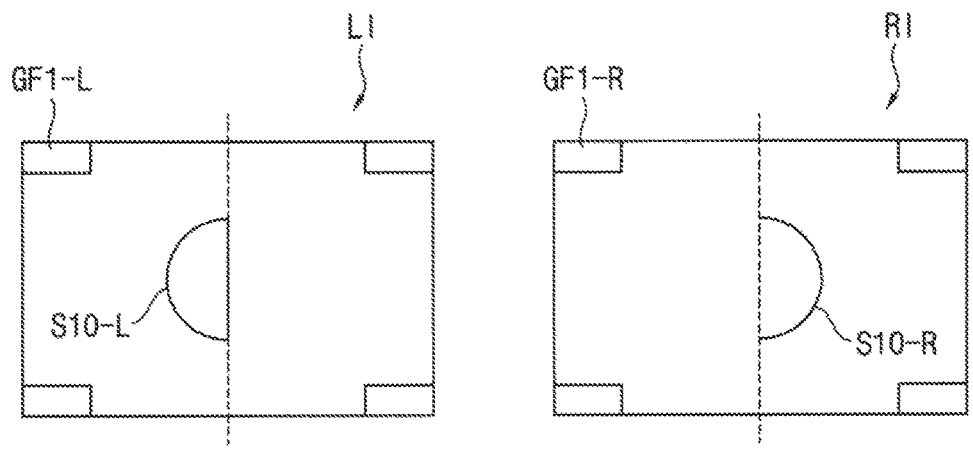
FIGS. 18 and 19 are diagrams illustrating examples of a binocular disparity adjustment image displayed on a display panel.
Figure 18:
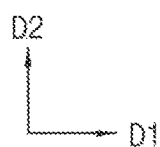
Figure 19:
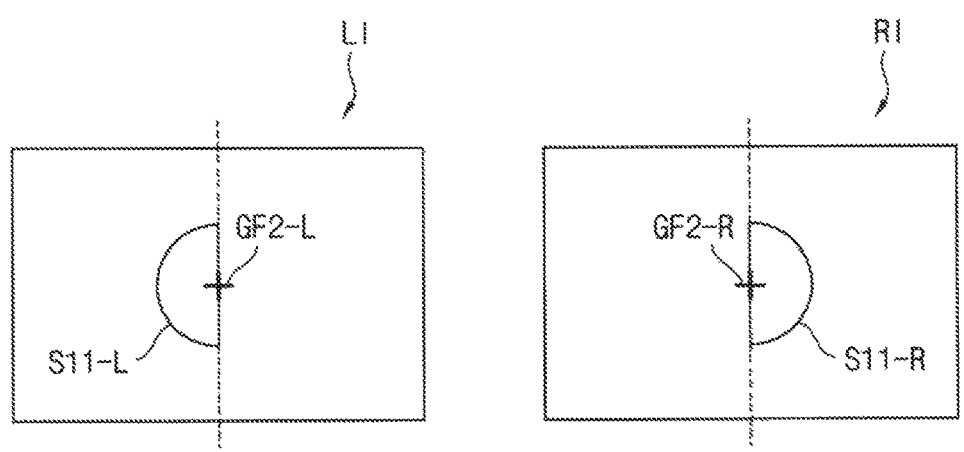
Figure 19:
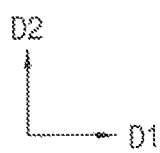

FIG. 13 is a flow chart illustrating another example of a method of deriving a binocular disparity adjustment data SD in a method of driving a head mounted display of FIGS. 5A and 5B. FIGS. 14A and 14B are diagrams illustrating one example of a binocular position adjustment image displayed on a display panel. FIGS. 15A and 15B are diagrams illustrating another example of a binocular position adjustment image displayed on a display panel. FIGS. 16A and 16B are diagrams illustrating still another example of a binocular position adjustment image displayed on a display panel. FIGS. 17A and 17B are diagrams illustrating still another example of a binocular position adjustment image displayed on a display panel. FIGS. 18 and 19 are diagrams illustrating examples of a binocular disparity adjustment image displayed on a display panel.

Referring to FIGS. 13 through 19, the binocular disparity adjustment data SD may be derived by performing the binocular disparity test operations (e.g., a binocular position perception test operation, a binocular size perception test operation, or a binocular luminance perception test operation). The method of deriving the binocular disparity adjustment data SD according to the present exemplary embodiment is substantially the same as the method of the exemplary embodiment described in FIG. 6, except that the operation of adjusting a position of a right-eye image with respect to a left-eye image in a second direction. Therefore, the same reference numerals will be used to refer to the same or like parts as those described in the previous exemplary embodiment of FIG. 6, and any repetitive explanation concerning the above elements will be omitted.

A first binocular position perception test operation may be performed to adjust the position of the right-eye with respect to the left-eye in the first direction D1 (S210).

As shown in FIG. 14A, the head mounted display may display a left-eye image LI including a sixth left-eye object S6-L on the left-eye panel region and a right-eye image RI including a sixth right-eye object S6-R on the right-eye panel region. For example, the sixth left-eye object S6-L may be a red color straight line extending in the second direction D2 and may be disposed on the center of the left-eye image LI. The sixth right-eye object S6-R may be a cyan color circle having a visual angle of about 1 degree and may be disposed on the center of the right eye image RI or deviated from the center of the right eye image RI and disposed on the right side of the center, for example.

As shown in FIG. 14B, the user may move the right-eye image RI in a first direction D1 using an input device, thus, the x-axis value of the position of the right-eye image RI corresponding to the first direction D1 may be increased or decreased, such that the sixth left-eye object S6-L overlaps the center point of the moved sixth right-eye object S6-R'. The position adjustment data can be generated based on a distance that the right-eye image RI has been moved in the first direction D1.

A second binocular position perception test operation may be performed to adjust the position of the right-eye with respect to the left-eye in the second direction D2 (S220).

In one example embodiment, as shown in FIG. 15A, the head mounted display may display a left-eye image LI including a seventh left-eye object S7-L on the left-eye panel region and a right-eye image RI including a seventh right-eye object S7-R on the right-eye panel region. For example, the seventh left-eye object S7-L may be an upper semicircle of a circle having a visual angle of about 5 to about 10 degrees and may be disposed on the upper side of the center of the left-eye image LI. The seventh right-eye object S7-R may be a lower semicircle of a circle having a visual angle of about 5 to about 10 degrees and may be disposed on the lower right side of the center of the right-eye image RI.

As shown in FIG. 15B, the user may move the right-eye image RI in the first direction D1 and the second direction D2 using the input device such that the moved seventh right-eye object S7-R' and the seventh left-eye object S7-L are recognized as a single circle. The position adjustment data can be generated based on a distance that the right-eye image RI has been moved in the first direction D1 and the second direction D2.

In another example embodiment, as shown in FIG. 16A, in the second binocular position perception test operation, the head mounted display may display a left-eye image LI including an eighth left-eye object S8-L on the left-eye panel region and a right-eye image RI including an eighth right-eye object S8-R on the right-eye panel region. For example, the eighth left-eye object S8-L may be a right arrow shape and may be disposed on the left side of the center of the left-eye image LI. The eighth right-eye object S8-R may be a left arrow shape and may be disposed on the right side of the center of the right-eye image RI.

As shown in FIG. 16B, the user may move the right-eye image RI in the first direction D1 and the second direction D2 using the input device such that the moved eighth right-eye object S8-R' and the eighth left-eye object S8-L are contact with each other at arrowhead. The position adjustment data can be generated based on a distance that the right-eye image RI has been moved in the first direction D1 and the second direction D2.

In still another example embodiment, as shown in FIG. 17A, in the second binocular position perception test operation, the head mounted display may display a left-eye image LI including an ninth left-eye object S9-L on the left-eye panel region and a right-eye image RI including an ninth right-eye object S9-R on the right-eye panel region. For example, the ninth left-eye object S9-L and the ninth right-eye object S9-R may have an L-shape. The ninth left-eye object S9-L and the ninth right-eye object S9-R may be in a point symmetry. The ninth left-eye object S9-L may be disposed in the upper left of the center of the right-eye image RI and the ninth right-eye object S9-R may be disposed in the lower right of the center of the right-eye image RI As shown in FIG. 17B, the user may move the right-eye image RI in the first direction D1 and the second direction D2 using the input device such that corners of the moved ninth right-eye object S9-R' and the ninth left-eye object S9-L are contact with each other. The position adjustment data can be generated based on a distance that the right-eye image RI has been moved in the first direction D1 and the second direction D2.

A binocular size perception test operation may be performed to adjust the size ratio of the right-eye image with respect to the left-eye image (S230). Since the method of adjusting the size of the right-eye image with respect to the left-eye image is described above, duplicated descriptions will be omitted.

In one example embodiment, in the binocular position adjustment image or the binocular size adjustment image, the left-eye image may further include a first guide object of which position does not changed regardless of the input signal, the right-eye image may further include a second guide object of which position does not changed regardless of the input signal, and the first guide object and the second guide object may be disposed at positions corresponding to each other. Accordingly, because the user can adjust the relative position or the relative size of the first object and the second object on the basis of the first and second guide objects, the position adjustment data or the size adjustment data may be derived more accurately.

In one example, as shown in FIG. 18, the left-eye image LI may include a first guide object GF1-L having four black square shapes located at four corners and a tenth left-eye object S10-L. The right-eye image RI may include a second guide object GF1-R having four black square shapes located at four corners and a tenth right-eye object S10-R. In another example, as shown in FIG. 19, the left-eye image LI may include a first guide object GF2-L having a '+'-shape at the center of the left-eye image LI and an eleventh left-eye object S11-L. The right-eye image RI may include a second guide object GF2-R having a '+'-shape at the center of the right-eye image RI and an eleventh right-eye object S11-R.

A left-eye luminance perception test operation for measuring a luminance difference perception degree of the left-eye may be performed (S250), and then a right-eye luminance perception test operation for measuring a luminance difference perception degree of the right-eye may be performed (S260). Since the methods of the luminance difference perception degree of the left-eye or the right-eye, are described above, duplicated descriptions will be omitted.

Figure 20:
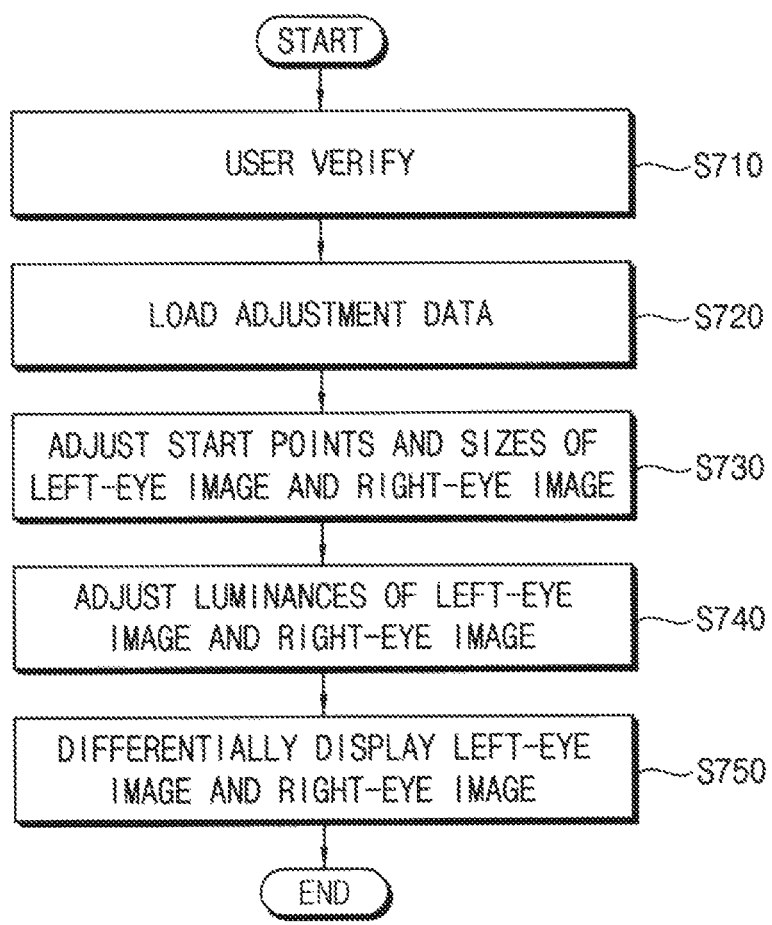
FIG. 20 is a flow chart illustrating an example of a method of differently displaying an image on a left-eye panel region and a right-eye panel region in a method of driving a head mounted display of FIGS. 5A and 5B.

FIG. 20 is a flow chart illustrating an example of a method of differently displaying an image on a left-eye panel region and a right-eye panel region in a method of driving a head mounted display of FIGS. 5A and 5B.

Referring to FIG. 20, in the method of driving a head mounted display, the user wearing the head mounted display may be verified to differentially drive a left display panel (i.e., the left-eye region) and a right display panel (i.e., a right-eye region) (S710). For example, the head mounted display may sense biometric information (e.g., iris information, fingerprint information, etc.) of the user and may search the user information corresponding to the sensed biometric information from the user information storage (not shown) (e.g., user information database management system).

The head mounted display may load the adjustment data for the verified user (S720). For example, the head mounted display may search and load the position adjustment data, the size adjustment data, and the luminance adjustment data corresponding to the verified user from the adjustment data storage.

The head mounted display may adjust a start point and a size of at least one of left-eye image or right-eye image based on the position adjustment data and the size adjustment data (S730).

In one example embodiment, a size of at least one of an input left-eye image or an input right-eye image included in image source may be adjusted based on the size adjustment data. For example, the size adjustment data may include a scaling factor indicating a ratio of a size of the adjusted image to a size of the original image. The size of the left-eye image after the adjustment may be calculated according to [Equation 1].

$$WLa = WLb * SFLw,$$

$$HLa = HLb * SFLh \qquad \text{[Equation 1]}$$

Here, WLa indicates a width of the left-eye image after the adjustment, WLb indicates a width of the left-eye image before the adjustment, SFLw indicates a scaling factor for a width of the left-eye image, HLa indicates a height of the left-eye image after the adjustment, HLb indicates a height of the left-eye image before the adjustment, SFLh indicates a scaling factor for a height of the left-eye image.

In the same way, the size of the right-eye image after the adjustment may be calculated according to [Equation 2].

$$WRa = WRb * SFRw,$$

$$HRa = HRb * SFRh \qquad \text{[Equation 2]}$$

Here, WRa indicates a width of the right-eye image after the adjustment, WRb indicates a width of the right-eye image before the adjustment, SFRw indicates a scaling factor for a width of the right-eye image, HRa indicates a height of the right-eye image after the adjustment, HRb indicates a height of the right-eye image before the adjustment, SFRh indicates a scaling factor for a height of the right-eye image.

In one example embodiment, a start point of at least one of the left-eye image or the right-eye image may be adjusted based on the position adjustment data and the size adjustment data. For example, the position adjustment data may include a position shift value of a right-eye image with respect to a left-eye image. Both of the input left-eye image and the input right-eye image may be move by an amount of half of the position shift value in opposite direction, respectively. In this case, the start point of the left-eye image after the adjustment may be calculated according to [Equation 3].

$$PSLx=PCLx-WLa/2+(SDx/2),$$

$$PSLy=PCLy-HLa/2+(SDy/2) \quad \text{[Equation 3]}$$

Here, PSLx indicates x-value of the start point of the left-eye image after the adjustment, PCLx indicates x-value of the center point of the left-eye image before the adjustment, WLa indicates a width of left-eye image after the adjustment, SDx indicates x-value of a position shift value, PSLy indicates y-value of the start point of the left-eye image after the adjustment, PCLy indicates y-value of the center point of the left-eye image before the adjustment, HLa indicates a height of left-eye image after the adjustment, SDy indicates y-value of the position shift value.

In the same way, the start point of the right-eye image after the adjustment may be calculated according to [Equation 4].

$$PSRx=PCRx-WRa/2-(SDx/2),$$

$$PSRy=PCRy-HRa/2-(SDy/2) \quad \text{[Equation 4]}$$

Here, PSRx indicates x-value of the start point of the right-eye image after the adjustment, PCRx indicates x-value of the center point of the right-eye image before the adjustment, WRa indicates a width of right-eye image after the adjustment, SDx indicates x-value of a position shift value, PSRy indicates y-value of the start point of the right-eye image after the adjustment, PCRy indicates y-value of the center point of the right-eye image before the adjustment, HRa indicates a height of right-eye image after the adjustment, SDy indicates y-value of the position shift value.

The head mounted display may adjust a luminance of at least one of left-eye image or right-eye image based on the luminance adjustment data (S740). The luminance adjustment data may be generated based on a difference between the left-eye luminance perception data and the right-eye luminance perception data. An adjustment value corresponding to the luminance adjustment data may be derived using the look-up table. The adjustment value may be applied to the input left-eye image or the input right-eye image to adjust the luminance. For example, when the left-eye luminance perception data is greater than the right-eye luminance perception data (i.e., when the left-eye responds more sensitively to luminance than the right-eye), the luminance perceived by both eyes may be adjusted to substantially the same level by increasing the luminance of the right-eye image with respect to the luminance of the left-eye image or by decreasing the luminance of the left-eye image with respect to the luminance of the right-eye image. In this time, the luminance of the left-eye image and the luminance of the right-eye image may be adjusted by various dimming methods such as a method of adjusting the image data, a method of changing the gamma curve, a method of adjusting the emission duration time, etc.

The head mounted display may differentially display the left-eye image and the right-eye image (S750). Thus, the head mounted display may display the adjusted image generated by differentially adjusting the left eye image and the right eye image according to the characteristics of user's eyes on the left-eye panel region (i.e., left panel region) and the right-eye panel region (i.e., right panel region).

Unlike the three-dimensional (3D) display, the head-mounted display independently outputs the left-eye image and the right-eye image. Accordingly, cross talk may not occur in the head-mounted display. Therefore, the binocular disparity can be accurately leveled or quantified according to the binocular difference. In result, the head-mounted display may display the left-eye image and the right-eye image that are differentially adjusted according to the characteristics of user's eyes on the left-eye panel region and the right-eye panel region, respectively. It is possible to secure user accessibility through universal design and to reduce fatigue of the user.

Although a method of driving head mounted display and a head mounted display performing the method according to example embodiments have been described with reference to figures, those skilled in the art will readily appreciate that many modifications are possible in the example embodiments without materially departing from the novel teachings and advantages of the present inventive concept. For example, the left-eye object may be deviated from the center of the left-eye image LI. In this case, the user may move the left-eye object in the first direction D1 and the second direction D2 using the input device such that the left-eye object can be disposed at the center of the left-eye image LI. When both of the left-eye object and the right-eye object are deviated from the center of the left-eye image LI and the center of the right-eye image RI, the user may move the left-eye object and the right-eye object in the first direction D1 and the second direction D2 using the input device such that the left-eye object and the right-eye object can be disposed at the center of the left-eye image LI and the right-eye image RI.

The present inventive concept may be applied to an electronic device having the display device. For example, the present inventive concept may be applied to a head mounted display, a smart phone, a smart pad for providing VR (virtual reality) experience.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A method of driving a head mounted display comprising:
    deriving a position adjustment data by displaying a binocular position adjustment image on a left-eye panel region and a right-eye panel region;
    deriving a size adjustment data by displaying a binocular size adjustment image on the left-eye panel region and the right-eye panel region, the size adjustment data including a scaling factor indicating a ratio of a size of the adjusted image to a size of the original image;
    generating a luminance adjustment data based on a difference between a left-eye luminance perception data and a right-eye luminance perception data, wherein one of a left-eye luminance perception image and a right-eye luminance perception image includes a plurality of achromatic rectangles having a plurality of grayscale values each of which has a fixed gray scale values during the generating of the luminance adjustment data, and the other of the left-eye luminance perception image and the right-eye luminance perception image includes a background image having a fixed grayscale value and a test object having a grayscale value subject to change during the generating of the luminance adjustment data;

converting an image source into an input image data based on at least one of the position adjustment data, the size adjustment data, or the luminance adjustment data; and displaying an image corresponding to the input image data on the left-eye panel region and the right-eye panel region.

2. The method of claim 1, further comprising:

displaying a binocular balancing image on the left-eye panel region and the right-eye panel region, wherein the binocular balancing image includes a first left-eye image and a first right-eye image, the first left-eye image including a first left-eye object and displayed on the left-eye panel region, the first right-eye image including a first right-eye object and displayed on the right-eye panel region.

3. The method of claim 1, wherein the deriving the position adjustment data includes:

displaying a second left-eye image including a second left-eye object on the left-eye panel region and a second right-eye image including a second right-eye object on the right-eye panel region;

moving at least one of the second left-eye image or the second right-eye image in a first direction or a second direction orthogonal to the first direction based on an input signal received from an input device; and generating the position adjustment data based on a moved position to which the at least one of the second left-eye image or the second right-eye image is moved.

4. The method of claim 3, wherein a first color of the second left-eye object is complementary to a second color of the second right-eye object.

5. The method of claim 3, wherein the second left-eye object and the second right-eye object have different sizes and have shapes substantially the same to each other.

6. The method of claim 3, wherein the second left-eye object and the second right-eye object are symmetrical with each other and have the same size.

7. The method of claim 3, wherein the second left-eye image further includes a first guide object of which position does not change regardless of the input signal, wherein the second right-eye image further includes a second guide object of which position does not changed regardless of the input signal, and wherein the first guide object and the second guide object are disposed at positions corresponding to each other.

8. The method of claim 1, wherein the deriving the size adjustment data includes:

displaying a third left-eye image including a third left-eye object on the left-eye panel region and a third right-eye image including a third right-eye object on the right-eye panel region;

scaling at least one of the third left-eye image or the third right-eye image in a first direction or in a second direction orthogonal to the first direction based on an input signal received from an input device; and generating the size adjustment data based on a scaled size to which the at least one of the third left-eye image or the third right-eye image is scaled.

9. The method of claim 8, wherein the third left-eye object and the third right-eye object are symmetrical with each other and have the same size.

10. The method of claim 1, wherein the generating the luminance adjustment data includes:

deriving the left-eye luminance perception data by displaying the left-eye luminance perception image on the left-eye panel region, and deriving the right-eye luminance perception data by displaying the right-eye luminance perception image on the right-eye panel region, and wherein the deriving the left-eye luminance perception data includes:

displaying a fourth left-eye image including a fourth left-eye object on the left-eye panel region and a fourth right-eye image on the right-eye panel region;

gradually increasing or decreasing a grayscale of the fourth left-eye object; and generating the left-eye luminance perception data based on the grayscale of the fourth left-eye object at a time point when an input signal is received from an input device.

11. The method of claim 10, wherein the fourth left-eye image includes the background image having a first grayscale value, and wherein the grayscale of the fourth left-eye object is increased or decreased every predetermined period from the first grayscale value.

12. The method of claim 10, wherein the fourth right-eye image includes a fourth right-eye object including a plurality of rectangular shapes having the plurality of grayscale values.

13. The method of claim 10, wherein the deriving the right-eye luminance perception data includes:

displaying a fifth left-eye image on the left-eye panel region and a fifth right-eye image including a fifth right-eye object on the right-eye panel region;

gradually increasing or decreasing a grayscale of the fifth right-eye object; and generating the right-eye luminance perception data based on the grayscale of the fifth right-eye object at a time point when the input signal is received.

14. The method of claim 1, wherein the converting the image source into the input image data includes:

adjusting a size of at least one of an input left-eye image or an input right-eye image included in the image source based on the size adjustment data;

adjusting a display starting point of at least one of the input left-eye image or the input right-eye image based on the position adjustment data and the size adjustment data; and adjusting a luminance of at least one of the input left-eye image or the input right-eye image based on the luminance adjustment data.

15. A method of driving a head mounted display comprising:

deriving a binocular disparity adjustment data by displaying a binocular disparity adjustment image on a left-eye panel region and a right-eye panel region;

generating an input image data by adjusting at least one of an input left-eye image displayed on the left-eye panel region or an input right-eye image displayed on the right-eye panel region based on the binocular disparity adjustment data; and displaying an image corresponding to the input image data on the left-eye panel region and the right-eye panel region, wherein deriving the binocular disparity adjustment data includes deriving a size adjustment data by displaying a binocular size adjustment image on the left-eye panel region and the right-eye panel region, the size adjustment data including a scaling factor indicating a ratio of a size of the adjusted image to a size of the original image, and generating a luminance adjustment data based on a difference between a left-eye luminance perception data and a right-eye luminance perception data, and wherein one of a left-eye luminance perception image and a right-eye luminance perception image includes a plurality of achromatic rectangles having a plurality of grayscale values each of which has a fixed gray scale value during the generating of the luminance adjustment data, and the other of the left-eye luminance perception image and the right-eye luminance perception image includes a background image having a fixed grayscale value and a test object having a grayscale value subject to change during the generating of the luminance adjustment data.

16. The method of claim 15, wherein the binocular disparity adjustment data includes at least one of a position shift value, a size ratio, or a luminance ratio of a right-eye image with respect to a left-eye image.

17. The method of claim 15, wherein deriving the binocular disparity adjustment data further includes:
displaying a binocular balancing image on the left-eye panel region and the right-eye panel region;
deriving a position adjustment data by displaying a binocular position adjustment image on the left-eye panel region and the right-eye panel region;
deriving a left-eye luminance perception data by displaying the left-eye luminance perception image on the left-eye panel region;
deriving a right-eye luminance perception data by displaying the right-eye luminance perception image on the right-eye panel region; and
generating a luminance adjustment data based on a difference between the left-eye luminance perception data and the right-eye luminance perception data.

* * * * *